(12) United States Patent
Maes et al.

(10) Patent No.: US 7,255,986 B2
(45) Date of Patent: Aug. 14, 2007

(54) COMPOSITIONS FOR THE DIAGNOSIS AND TREATMENT OF EPIZOOTIC CATARRHAL ENTERITIS IN FERRETS

(75) Inventors: Roger K. Maes, Okemos, MI (US); Annabel G. Wise, Bath, MI (US); Matti Kiupel, Laingsburg, MI (US)

(73) Assignee: The Board of Trustees Operating Michigan State University, Lansing, MI (US)

( * ) Notice: Subject to any disclaimer, the term of this patent is extended or adjusted under 35 U.S.C. 154(b) by 36 days.

(21) Appl. No.: 10/354,606

(22) Filed: Jan. 30, 2003

(65) Prior Publication Data

US 2004/0038202 A1 Feb. 26, 2004

Related U.S. Application Data

(60) Provisional application No. 60/353,608, filed on Jan. 31, 2002.

(51) Int. Cl.
| | |
|---|---|
| C12Q 1/70 | (2006.01) |
| C12Q 1/68 | (2006.01) |
| C12P 21/06 | (2006.01) |
| C12N 21/00 | (2006.01) |
| C12N 5/00 | (2006.01) |
| C07K 1/00 | (2006.01) |

(52) U.S. Cl. .............................. 435/5; 435/6; 435/69.1; 435/320.1; 435/325; 530/388.3; 530/350; 536/23.72

(58) Field of Classification Search ................ 435/5, 435/69.1
See application file for complete search history.

(56) References Cited

U.S. PATENT DOCUMENTS

| | | | |
|---|---|---|---|
| 4,366,241 A | 12/1982 | Tom et al. ..................... 435/7 |
| 4,435,504 A | 3/1984 | Zuk et al. ..................... 435/7 |
| 4,657,760 A | 4/1987 | Kung et al. ................... 424/85 |
| 4,683,195 A | 7/1987 | Mullis et al. .................. 435/6 |
| 4,683,202 A | 7/1987 | Mullis ........................ 435/91 |
| 4,946,778 A | 8/1990 | Lander et al. ................ 435/69 |
| 4,965,188 A | 10/1990 | Mullis et al. .................. 435/6 |
| 5,096,815 A | 3/1992 | Lander et al. ............. 435/69.1 |
| 5,198,346 A | 3/1993 | Lander et al. ............. 435/69.1 |
| 5,206,344 A | 4/1993 | Katre et al. ................. 530/351 |
| 5,223,409 A | 6/1993 | Lander et al. ............. 435/69.7 |
| 5,225,212 A | 7/1993 | Martin et al. ............... 424/450 |

(Continued)

FOREIGN PATENT DOCUMENTS

EP 1033405 A2 * 9/2000

(Continued)

OTHER PUBLICATIONS

The Sanger Center et al., "Toward a Complete Human Genome Sequence," Genome Research, pp. 1097-1108 (1998).*

(Continued)

*Primary Examiner*—Bruce R. Campell
*Assistant Examiner*—M. Franco Salvoza
(74) *Attorney, Agent, or Firm*—Medlen & Carroll, LLP

(57) ABSTRACT

The present invention relates to the use of novel nucleotide sequences for the M and N region peptide of the ferret coronavirus and derivative products for the diagnosis and treatment of epizootic catarrhal enteritis (ECE) in ferrets.

7 Claims, 10 Drawing Sheets

SEQ ID NO:1  Bases 001-377 encompass the 3' end of the M gene region.
Bases 378-735 encompass the 5' end of the N gene region.

```
  1  GACTAGTTGG TGGAGTTTTA ACCCTGAAAC CAACGCAATC TTGTGTCTTA GTGCAGTAGG
 61  AAAAAGATTT GTATTACCAC TAAATGGTGC GCCTACAGGT GTTACGTTGA CACTTTTGTC
121  AGGTAACTTA TATGCTGAAG GCTTCAAGGT TGGAAGTGGT GTAAATGTCG ATAACCTACC
181  CAAGTACATT ATGGTAGCCA CACCTGGTAA TACTATTATA TATCACCAAG TTGGCAAGTC
241  TCTTAAAGCA TCCAGTGCGA CTGGTTGGTC ATACTATGTC CGAGCTAAAG CAGGCGATTA
301  CTCAACAGAA GCAAGACAAG ATCATTTGAG TGAACACGAA AAACTGTTAC ATATGGTATA
361  AGAACTAAAC TTCTATCATG GCTGGAAACG GACAACGTGT TAACTGGGGG GACGAACCTG
421  CTCCTTCACA GAAGCGTGGT CGTTCTCGTT CCCGTTCCCG CCGTAATGCT GATATACCAT
481  TGTCATATTT CAACCCTATT ACCCATGAAG GTAAGAAGCC CTTTTGGACT GTAGCACCAA
541  AAGATTTCGT GCCTATTGGT AAGGGAAATA AGGACCAACA AGTAGGTTAT TGGAATAGAC
601  AGCAACGTTA CCGCATTCAA AAGGGTCAAA AAGTGGACTT ACCAGACAGG TGGTTCTTTT
661  ACTACCTAGG AACTGGTCCA CATAGCAATG CTAAATTTAA GGACCGTATT GAAGGAGTCT
721  TCTGGGTCGC TCGAG
```

U.S. PATENT DOCUMENTS

| | | | | |
|---|---|---|---|---|
| 5,474,796 A | | 12/1995 | Brennan | 435/287 |
| 5,538,848 A | | 7/1996 | Livak et al. | 435/6 |
| 5,584,807 A | | 12/1996 | McCabe | 604/71 |
| 5,656,275 A | * | 8/1997 | Wasmoen et al. | 424/199.1 |
| 5,780,266 A | * | 7/1998 | Dale et al. | 435/69.3 |
| 6,747,137 B1 | * | 6/2004 | Weinstock et al. | 536/23.1 |
| 6,812,339 B1 | * | 11/2004 | Venter et al. | 536/24.31 |

FOREIGN PATENT DOCUMENTS

| | | |
|---|---|---|
| WO | WO 90/08832 | 8/1990 |
| WO | WO 93/03176 | 2/1993 |
| WO | WO 93/03367 | 2/1993 |
| WO | WO 99/67641 | 12/1999 |
| WO | WO 00/39587 | 7/2000 |
| WO | WO 200171042 A2 * | 9/2001 |

OTHER PUBLICATIONS

Mcgoldrick et al., "Characterisation of a recent virulent transmissible gastroenteritis virus from Britain with a deleted ORF 3a," Arch Virol 144. pp. 763-770 (1999).*

Results 1, 11, 16.rge; Results 4-7, 10-12, 16.rng; Result 1, 16.rni.*

Ben-Bassat et al.,"Processing of the Initiation methionine from proteins: properties of *Escherichia coli* methionine aminopeptidase and its gene structure," *J. Bacteriol.*, 169:751-757 (1987).

Bradley et al. "Formation of germ-line chimaeras from embryo-derived teratocarcinoma cell lines," *Nature* 309:255-256 (1984).

Brinster et al., "Factors affecting the efficiency of introducing foreign DNA into mice by microinjecting eggs," *Proc. Natl. Acad. Sci. USA* 82:4438-4442 (1985).

Caldwell and Joyce, "Radomization of genes by PCR mutagenesis," *PCR Methods Appl.*, 2:28-33 (1992).

Caruthers et al.,"New Chemical Methods for Synthesizing Polynucleotides" *Nucl. Acids Res.*, 7:215-223 (1980).

Chamberlain et al.,"New RNA polymerase from *Escherichia coli* infected with bacteriophage T7," *Nature*, 228:227-231 (1970).

Chow et al.,"Synthesis of oligodeoxyribonucleotides on silica gel support," *Nucl. Acids Res.* 9:2807-2817 (1981).

Cole et al. (1985) in *Monoclonal Antibodies and Cancer Therapy*,"The EBV-hybridoma techique and its application to human lung cancer," Alan R. Liss, Inc., pp. 77-96.

Cote et al.,"Generation of human monoclonal antibodies reactive with cellular antigens," *Proc. Natl. Acad. Sci. USA*, 80:2026-2030 (1983).

Crameri et al., "Improved green fluorescent protein by molecular evolution using DNA shuffling," *Nat. Biotech.*, 12:315-319 (1996).

Crameri et al.,"Molecular evolution of an arsenate detoxification pathway by DNA shuffling," *Nat. Biotech.*, 15:436-438 (1997).

Crea and Horn,"Synthesis of oligonucleotides on cellulose by a phosphotriester method,"*Nucl. Acids Res.*, 9:2331-2348 (1980).

Cwirla et al., *"Peptides on phage: a vast library of peptides for indentifying ligands,"* *Proc. Natl. Acad. Sci. USA*, 87:6378-6382 (1990).

Dafforn et al.,"Rapid,simple, and reliable doctor's office test for antibodies of human immunodeficiency virus I in serum," *Clin. Chem.* 36:1312-1316 (1990).

Devlin et al., "Random peptide libraries: a source of specific protein binding molecules," *Science* 249:404-406 (1990).

deWet et al.,"Firefly luciferase gene: structure and expression in mammalian cells," *Mol. Cell. Biol.* 7:725-737 (1987).

Eckert and Kunkel,"DNA polymerase fidelity and the polymerase chain reaction," *PCR Methods* App., 1:17-24 (1991).

Evans and Kaufman, "Establishment in culture of pluripotential cells from mouse embryos" *Nature* 292:154-156 (1981).

Evans et al.,"An engineered poliovirus chimaera elicits broadly reactive HIV-1 neutralizing antibodies," *Nature* 339:385-388 (1989).

Gleba et al.,"Use of plant roots for phytoremediation and molecular farming," *Proc. Natl. Acad. Sci. U.S.A,*. 96:5973-5977 (1999).

Gluzman,"SV40-transformed simian cells support the replication of early SV40 mutants," *Cell* 23:175-182 (1981).

Gossler et al., "Transgenesis by means of blastocyst-derived embryonic stem cell lines," *Proc. Acad. Sci. USA*, 83:9065-9069 (1986).

* cited by examiner

SEQ ID NO:1 Bases 001-377 encompass the 3' end of the M gene region.
Bases 378-735 encompass the 5' end of the N gene region.

```
1   GACTAGTTGG TGGAGTTTTA ACCCTGAAAC CAACGCAATC TTGTGTCTTA GTGCAGTAGG
61  AAAAAGATTT GTATTACCAC TAAATGGTGC GCCTACAGGT GTTACGTTGA CACTTTTGTC
121 AGGTAACTTA TATGCTGAAG GCTTCAAGGT TGGAAGTGGT GTAAATGTCG ATAACCTACC
181 CAAGTACATT ATGGTAGCCA CACCTGGTAA TACTATTATA TATCACCAAG TTGGCAAGTC
241 TCTTAAAGCA TCCAGTGCGA CTGGTTGGTC ATACTATGTC CGAGCTAAAG CAGGCGATTA
301 CTCAACAGAA GCAAGACAAG ATCATTTGAG TGAACACGAA AAACTGTTAC ATATGGTATA
361 AGAACTAAAC TTCTATCATG GCTGGAAACG GACAACGTGT TAACTGGGGG GACGAACCTG
421 CTCCTTCACA GAAGCGTGGT CGTTCTCGTT CCCGTTCCCG CCGTAATGCT GATATACCAT
481 TGTCATATTT CAACCCTATT ACCCATGAAG GTAAGAAGCC CTTTTGGACT GTAGCACCAA
541 AAGATTTCGT GCCTATTGGT AAGGGAAATA AGGACCAACA AGTAGGTTAT TGGAATAGAC
601 AGCAACGTTA CCGCATTCAA AAGGGTCAAA AAGTGGACTT ACCAGACAGG TGGTTCTTTT
661 ACTACCTAGG AACTGGTCCA CATAGCAATG CTAAATTTAA GGACCGTATT GAAGGAGTCT
721 TCTGGGTCGC TCGAG
```

FIG. 1

SEQ ID NO:4 Bases 001-628 encompass a Spike gene region.

```
1   TGGATAAGGT TAATGAGTGC GTGCGTTCAC AGTCTAGTAG GTTTGGTTTC TGTGGCAACG
61  GCACTCACTT GTTTTCTTTA GCTAATGCTG CACCTAGTGG TATCATGCTA TTTCATACAG
121 TCCTAGTGCC CACGTCTTAC ACAAGTGTAA CAGCGTGGTC TGGCATTTGT TTTGATAACG
181 TTGGTTTGAT TGTCAAGGAT GTTTCGTTGA CGTTGTTTAA AACTCATGAT GATAAATTCT
241 ACTTGACACC ACGTACTATG TATGAGCCGC GTGTCGCGAC TAGCGCAGAT TTCGTGCGAA
301 TTAATAGCTG TGCCACTACT TTTGTTAATG CCACTGCTAC AGAGCTACCT AATATTATAC
361 CTGATTATAT TGATGTTAAT AAGACAGTCC AAGACATGCT AGAGCAGTAT AAGCCCAATT
421 GGACAGTACC AAATTTATCC CTTGACTTGT TCAATCTAAC ATACTTAAAT CTCACGGGTG
481 AGATTAATGA TTTGGAGAAC AGGTCTGCTA CCTTGCAACA AACTGTTGTC GAATTACAGG
541 TTTTAATTGA TAATATTAAT GGAACTCTTG TAAATCTTGA GTGGCTTAAC ACAATTGAAA
601 CATACGTTAA GTGGCCATGG TACGTCTG
```

FIG 1 (Cont.)

SEQ ID NO:2    Amino acid sequence corresponding to M gene region of SEQ ID NO:1

```
  1  TSWWSFNPET NAILCLSAVG KRFVLPLNGA PTGVTLTLLS GNLYAEGFKV GSGVNVDNLP
 61  KYIMVATPGN TIIYHQVGKS LKASSAT

SEQ ID NO:2   Amino acid sequence corresponding to M gene region of SEQ ID NO:1. Substitution candidates underlined.

```
1   TSWWSFNPET NAILCLSAVG KRFVLPLNGA PTGVTLTLLS GNLYAEGFKV GSGVNVDNLP
61  KYIMVATPGN TIIYHQVGKS LKASSATGWS YYVRAKAGDY STEARQDHLS EHEKLLHMV
```

SEQ ID NO:3   Amino acid sequence corresponding to N gene region of SEQ ID NO:1. Substitution candidates underlined.

```
1   MAGNGQRVNW GDEPAPSQKR GRSRSRSRRN ADIPLSYFNP ITHEGKKPFW TVAPKDFVPI
61  GKGNKDQQVG YWNRQQRYRI QKGQKVDLPD RWFFYYLGTG PHSNAKFKDR IEGVFWVAR
```

SEQ ID NO:5   Amino acid sequence corresponding to Spike gene region of SEQ ID NO:4. Substitution candidates underlined.

```
1   DKVNECVRSQ SSRFGFCGNG THLFSLANAA PSGIMLFHTV LVPTSYTSVT AWSGICFDNV
61  GLIVKDVSLT LFKTHDDKFY LTPRTMYEPR VATSADFVRI NSCATTFVNA TATELPNIIP
121 DYIDVNKTVQ DMLEQYKPNW TVPNLSLDLF NLTYLNLTGE INDLENRSAT LQQTVVELQV
181 LIDNINGTLV NLEWLNTIET YVKWPWYV
```

FIG. 3

SEQ ID NO:12    Bases 1-251 encompass a Pol gene region.

```
  1  ACTCAGTTGA ATCTGAAAATA TGCCATATCA GGTAAGGCAC
 41  GAGCTCCGTAC TGTTGGTGGT GTGTCACTTT TGTCAACTAT
 81  GACCACAAGA CAGTATCATC AGAAACACTT AAAGCCTATT
121  GCCGCCATGC GTAACGCTAC AGTTGTCATT GGTACAGCCA
161  AGTTTTACGG CGGATGGGAC GATATGTTAA AGAATTTGAT
201  GCGTGACGTT GATAAATGGCT GTCTTATGGG TTGGGATTAT
241  CCAAAATGTG A
```

FIG. 4

SEQ ID NO:15    Reverse complement of Spike region (SEQ ID NO:4)

```
  1  GGATAAGGTT AATGAGTGCG TGCGTTCACA GTCTAGTAGG
 41  TTTGGTTCCT GTGGCAACGG CACTCACTTG TTTTCTTTAG
 81  CTAATGCTGC ACCTAGTGGT ATCATGCTAT TTCATACAGT
121  CCTAGTGCCC ACGTCTTACA CAAGTGTAAC AGCGTGGTCT
161  GGCATTTGTT TTGATAAACGT TGGTTTGATT GTCAAGGATG
210  TTTCGTTGAC GTTGTTTAAA ACTCATGATG ATAAATTCTA
261  CTTGACACCA CGTACTATGT ATGAGCCGCG AGTCGCGACT
301  AGTGCAGATT TCGTGCGAAT TAATAGCTGT GCCACTACTT
341  TTGTTAATGC CACTGTTACA GATCTACCTA ATATTATACC
381  TGATTATATT GATGTTAATA AGACAGTCCA AGACATGCTA
421  GAGCAGTATA AGCCCAATTG GACAGTACCA AATTTATCCC
461  TTGACTTGTT CAATCTAACA TACTTAAATC TCACGGGTGA
501  GATTAACGAT TTGGAGAACA GGTCTGTCAC CTTGCAACAA
541  ACTGTTGTCG AATTACAGGC TTTAATTGCT AACATCAATG
601  GCACGCTTGT TAACCTTGAA TGGCTTAACA GAGTTGAAAC
641  ATATGTTAAG TGGCCATGGT ACGTATGG
```

FIG. 5

SEQ ID NO:16 - M region

```
  1  GACTAGTTGG TGGAGTTTTA ACCCTGAAAC CAACGCAATC TTGTGTCTTA GTGCAGTAGG
 61  AAAAGATTT GTATTACCAC TAAATGGTGC GCCTACAGGT GTTACGTTGA CACTTTGTC
121  AGGTAACTTA TATGCTGAAG GCTTCAAGGT TGGAAGTGGT GTAAATGTCG ATAACCTACC
181  CAAGTACATT ATGGTAGCCA CACCTGGTAA TACTATTATA TATCACCAAG TTGGCAAGTC
241  TCTTAAAGCA TCCAGTGCGA CTGGTTGGTC ATACTATGTC CGAGCTAAAG CAGGCGATTA
301  CTCAACAGAA GCAAGACAAG ATCATTTGAG TGAACACGAA AAACTGTTAC ATATGGTATA
361  AGAACTAAAC TTCTATC
```

FIG. 6A

SEQ ID NO:16 - N region

```
 378 ATGGCTGGAA ACGGACAACG TGTTAACTGG GGGGACGAAC CTGCTCCTTC ACAGAAGCGT
 438 GGTCGTTCTC GTTCCCGTTC CCGCCGTAAT GCTGATATAC CATTGTCATA TTTCAACCCT
 498 ATTACCCATG AAGGTAAGAA GCCCTTTTGG ACTGTAGCAC CAAAAGATTT CGTGCCTATT
 558 GGTAAGGGAA ATAAGGACCA ACAAGTAGGT TATTGGAATA GACAGCAACG TTACCGCATT
 618 CAAAAGGGTC AAAAAGTGGA CTTACCAGAC AGGTGGTTCT TTTACTACCT AGGAACTGGT
 678 CCACATAGCA ATGCTAAATT TAAGGACCGT ATTGACGGAG TTTTCTGGGT TGGAAAGAAT
 738 GGTGCTAAAA CTGTGCCTAC AGGATTAGGA ACGCGTGGCA CCAACCAACA GTCTCTTGAC
 798 CTTAAATTTG ATGGTAACGT GCCTAATGAT TTCAAATTAG AACAAAATGT TGGGTCTAGA
 858 AACAACTCTA GGTCTCGATC TAGAGGAAGG TCTAAGTCCA ACAATAGATC CAATAACAAT
 918 AACAGTAACA GTGGTGATAT TGCCACAGCT GTTGTTGCAG CTTTAGCTCA AATGGGTTTT
 978 GCTCCCAAAG ACACACAGAA GAATAAGTCC CGCTCTAAAT CTAGGGATAG GTCTAAATCC
1038 AGAGAAAAAC CTATTCCTAA CAATGAGAAC AAGCACTCAT GGAAGAAAAC ACCTGGTAAA
1098 GGAGAGGTCG AGTCTATGTT TGGAAACCGT AGACCTGAGG CAAATTTTGG CAATGCAGAC
1158 TTAGTTAAGG CTGGCAGTGC AGATATACAT TACCCCTCAAC TAGCTGAGAT GGTTCCTAGT
1218 AACGCCGCCA TTTTATTTGG AGGTGAGTGG ACTTCTAAAG AAGAGGGTGA TGATGTTGTC
1278 TTAACTGTTA AGTACAGTTA TAAAGTGCCT AAGGGTGATA AGACAACTGG ATTTTTGCAA
1338 CACATTAACG CCTACACAAA GCCTTCAGAT ATTGTCAAAG AACAACGTTC TCGATCTAAA
1398 TCCAGAGAAC GTCCTCAAAT CCCTGTACCT TCCAATAGTG CAGAGACTGA AAATTACACT
1458 GATGTGTTTG ATGAGAATGT TGAAATTATT GATGAACTAA ACTAA
```

FIG. 6B

SEQ ID NO:16 – 3' terminus of genome

```
1503 CCATTTCTAT GAGTTCTAGC TTAATAACAA TCTTTAGTGG TAAAATTGG TTTTCTCTAC
1563 CTAGATCTTT TAAAGATTGG ATAGTATCTA AAGTCATATT CAAGGCACCT GCTGGAGGCA
1623 AAGTCAAACC AGACTACCGC CGCAGAGCTT TGTTAAACAG TCATAACAAT CATGTTAATT
1683 CTATGTCTGT TAGTTCTGTC TCTTTTTCA AATTCTTTAG GGCAAGAAGA TGACAAGCAT
1743 CAACATCCCA CATATAAACTG GGAAAGATTA GATTATTTTG AAGGTTCCTA CATCGAAATT
1803 GATAAAATCTG TGATTTTATC ATTACCACTT GACGCCAAAT TACATTGTGG TTTGGTTGAT
1863 GGTGTTTTGT GCAAGTTCCC AGTTTTTGAA GCTGCATATG ATGATCATGT AGACTATTAT
1923 TTAGATGTAG ACTCACCTtT CTACAGGTTT GTGAACACCT TCTACGTGGC TAAATTCATA
1983 GATGGTAAGT TTGACAATCG TGCCACTCTG AAGTTTCTAC CACGTACTAG CAAAGACAAG
2043 ATGCTTGTTA TTGGTGTGG TCTCAATGAC CCTCTCTCTAG ACTTGCCTTT TGGTACCCAA
2103 ATCTATAAATG ATGTGGACAT GACTCTTAAA GTCGACCATG TGCCTTGCAC TAACAGACGG
2163 TATTTTGTTA AGTACTGTCC TGGTGGTCCC AATCATTTTT GCTTTAAAGA TAAATTGGTA
2223 ATCAGAAGGT TTAGAGCATT TTTCCCTGTG TCTAATAATA ATAAAATTGA ACATGTTGAT
2283 TTATAAGAAG ATCTTCGGGC GAGTACCGTT AGATCTACTC TTACACAGAA TGGTAAGCAC
2343 GTATCTATGT AGGGTGTAAG TAACTCATAG ATATATTAGG AAGTTTAGAT TGAACTAATC
2403 AATACTAGAT TGAAAAATTG AGAGTAATTT AAAGATCCGC TTAGACGAGC CAACAATGGA
2461 AGGGCTCAAC TTTTGGATAC TAGTCAACTT GTTT
```

FIG. 6C

SEQ ID NO:17 Amino acid sequence of FECV capsid gene

```
1   MAGNGQRVNW GDEPAPSQKR GRSRSRSRRN ADIPLSYFNP ITHEGKKPFW
    TVAPKDFVPI

61  GKGNKDQQVG YWNRQQRYRI QKGQKVDLPD RWFFYYLGTG PHSNAKFKDR
    IDGVFWVGKN

121 GAKTVPTGLG TRGTNQQSLD LKFDGNVPND FKLEQNVGSR NNSRSRSRGR
    SKSNNRSNNN

181 NSNSGDIATA VVAALAQMGF APKDTQKNKS RSKSRDRSKS REKPIPNNEN
    KHSWKKTPGK

241 GEVESMFGNR RPEANFGNAD LVKAGSADIH YPQLAEMVPS NAAILFGGEW
    TSKEEGDDVV

301 LTVKYSYKVP KGDKTTAFLQ HINAYTKPSD IVKEQRSRSK SRERPQIPVP
    SNSAETENYT

361 DVFDENVEII DELN.
```

FIG 7

COMPOSITIONS FOR THE DIAGNOSIS AND TREATMENT OF EPIZOOTIC CATARRHAL ENTERITIS IN FERRETS

The present application claims the benefit of the filing date of U.S. Provisional Application No. 60/353,608 filed Jan. 31, 2002, which is incorporated herein by reference in its entirety.

FIELD OF THE INVENTION

The present invention relates to novel nucleotide sequences related to the polymerase (pol) region and M, E, N and S genes of the ferret coronavirus and the translated peptide products, as well as methods and compositions derived therefrom. More specifically, the present invention relates to the use of these sequences and derivative products for the diagnosis and treatment of epizootic catarrhal enteritis (ECE) in ferrets.

BACKGROUND

In early 1994 a mysterious disease cropped up among domestic ferrets (*Mustela putorius furo*) and spread quickly, particularly in the show circuit. It was originally called "the greenies," but its official name is "epizootic catarrhal enteritis" (ECE). Early symptoms of the disease are vomiting followed by lethargy, diminished food intake, and a "drowsy" appearance. However, the disease is usually characterized by the sudden onset of bright green or yellowish diarrhea. The disease is believed to damage the mucosa (the delicate intestinal lining which is instrumental in absorbing nutrients and water into the body) resulting in diarrhea and excess mucous production. In severe cases there may be deep ulcerations and bleeding into the intestinal lumen. Stools can range from bright green, loose and slimy to dark red, black and tarry (possibly indicative of the presence of blood in the stool). This variation can make accurate diagnosis difficult. Additionally, mouth and stomach ulcers form in many, but not all, of the infected ferrets. Death of the afflicted animal is not uncommon. This disease is highly contagious and can be transmitted without direct contact. Currently, the disease costs ferret breeders and owners millions of dollars a year in health care costs and lost revenue.

Currently, there is no diagnostic test for ferret ECE. Instead, diagnosis is generally a process of exclusion of other disorders, i.e., differential diagnosis. Furthermore, there is no specific treatment for ECE in ferrets. Most ferrets with ECE are treated as though they have a non-specific gastrointestinal ailment by any of a number of treatment regimes. Such treatments include supportive measures such as oral, SC, or IV administration of fluids and electrolytes and oral administration of antimicrobials. If malabsorption develops, oral administration of prednisone and provision of highly digestible nutritional supplements have been tried with some success. However, the efficacy of the treatments vary from each other and from animal to animal making adequate treatment of the disease difficult often time with unsatisfactory results.

As can be seen from the foregoing, what is needed is a test for the accurate diagnosis of ECE and new methods of treatment of this disease.

SUMMARY OF THE INVENTION

The present invention generally relates to compositions and methods for the diagnosis and treatment of epizootic catarrhal enteritis (ECE) in ferrets. It is not intended that the present invention be limited to particular method of diagnosis and treatment. Although the present, invention is not limited to any particular mechanism, it is believed that the coronavirus is, the causative agent of ECE. The novel oligonucleotide sequences of the present invention are from the ferret coronavirus.

In one embodiment, the present invention contemplates an 1) isolated nucleic acid (SEQ ID NO: 4) encoding at least a portion of the spike peptide (SEQ ID NO: 5) the ferret coronavirus or encoded protein set forth in FIGS. 1 and 2 and an isolated nucleic acid (SEQ ID NO: 1) encoding at least a portion of the ferret coronavirus comprising a portion of the M and N peptides (SEQ ID NO: 2 and 3) set forth in FIGS. 1 and 2 and an isolated nucleic acid sequence (SEQ ID NO: 12) set forth in FIG. 4 encoding at least a portion of the ferret coronavirus pol gene, including native and mutant sequences (e.g., spike, pol and M and N region containing one or more polymorphisms) and an isolated nucleic acid sequence (SEQ ID NO: 16) set forth in FIG. 6 encoding the ferret coronavirus capsid gene. The portions (or fragments), as defined below, may range in size from ten nucleotide residues to the entire nucleotide sequence minus one nucleotide. In one embodiment, said portion is between 10 and 100 nucleotide residues. In a preferred embodiment, the portion is between 10 and 30 nucleotide residues. Such portions may be utilized as probes. Although the present invention is not limited to any particular mechanism and an understanding of the mechanism is not required to practice the present invention, the spike peptide is believed to interact with receptors present on small intestinal epithelial cells in the digestive tract of the afflicted animal and to be a major inducer of humoral immune responses. The peptide partly encoded by SEQ ID NO: 12 is believed to function as the viral polymerase. The nucleocapsid protein is beleived to be invloved in the induction of cell-mediated immunity. The M and N peptides are belived to play a role in viral assembly.

In another embodiment, said nucleotide sequence encodes a polypeptide fragment. It is not intended that the present invention be limited by the nature or size of the fragment. In yet another embodiment, said nucleic acid encodes a fusion protein. Additionally, the present invention relates to isolated sequences that comprise a mutation of the nucleotide sequence encoding the spike peptide, mutation of the nucleotide sequence encoding the portion of the coronavirus encoding the area around and including the M-N protein region (i.e., the M-N region peptide) or a mutation in SEQ ID NO: 12 encoding at least a portion of the pol gene.

It is not intended that the present invention be limited as to the specific nature of the nucleotide sequence encoding the peptides described above or portions thereof. In one embodiment, said nucleic acid is contained in a vector. In another embodiment, said vector is in a host cell. In yet another embodiment, said vector is in a transgenic animal. Additionally, said gene may integrate into the genome of the transgenic animal. In a particular embodiment, the transgenic animal of the present invention may be generated with the transgene contained in an inducible, tissue specific promotor.

The present invention also contemplates RNA transcribed from the above-indicated nucleotide sequence as well as protein (typically purified protein) translated from this RNA. Moreover, the present invention contemplates antibodies produced from immunizing with this translated protein.

The present invention also contemplates using the above-named compositions in diagnostic screening assays. In one embodiment, antibodies made to translation products of the present invention are bound to an assay plate. Samples are then added to the assay. The ferret coronavirus spike peptide, pol region peptide and M and N region peptide and their respective receptors, or portions thereof, if present in the sample, bind to the plate bound anti-spike peptide antibodies, anti-pol antibodies and anti-M and N region peptide antibodies. Bound antigens are then detected by methods known in the art such as, for example, with labeled antibodies (e.g., radiolabeled, fluorescently labeled, enzyme labeled, etc.).

The present invention also contemplates using the above-named compositions in screening assays. The present invention is not limited by the particular method of screening. In one embodiment cells, are used such as, but not limited to, transformed cell lines. In another embodiment, primary cells may be used. The present invention is not limited to the nature of the transfection construct. The transfection constructs utilized are the optimal constructs available for the cell line chosen at the time of setting up the assay. In one embodiment, the present invention contemplates screening suspected compounds (e.g., drug candidates) in a system utilizing transfected cell lines. In one embodiment, the cells are transfected transiently. In another embodiment, the cells are stably transfected. In yet another embodiment, translation products of the invention are used in a cell-free assay system. In yet another embodiment, antibodies generated to the translation products of the invention are used in immunoprecipitation assays or used in vivo.

Furthermore, the present invention is also used to identify spike peptide, pol region peptide and M or N region peptide binding partners and interactive proteins. In one embodiment, antibodies generated to translation products of the invention are used in immunoprecipitation experiments to isolate peptides that interact with the spike peptide, pol region peptide and M or N region peptide. In another embodiment, the invention is used to generate fusion proteins that are used to isolate interactive proteins. In yet another embodiment, screens are conducted using the yeast two-hybrid system.

In another embodiment, peptides of the invention are used in microchip assays. For example, the present invention contemplates a method of screening, comprising: a) providing in any order: i) a first solid support (e.g. microchip) comprising peptides or peptide fragments from a library of the species to be examined and ii) a peptide, or portion thereof, encoded by the DNA of SEQ ID NO:1, SEQ ID NO:4, SEQ ID NO: 12 or SEQ ID NO: 16, and; b) contacting said microassay microchips with said peptide under conditions such that binding occurs.

The present invention is also used to identify new homologs of the spike peptide, pol region peptide and M and N region peptide or natural mutations thereof. The present invention contemplates screening for homologs using standard molecular procedures. In one embodiment, screens are conducted using Northern and Southern blotting.

The present invention contemplates a method of screening a compound, said method comprising: a) providing in any order: i) a first group of cells comprising a recombinant expression vector, wherein said vector comprises at least a portion of the oligonucleotide sequence of SEQ ID NO: 1, SEQ ID NO: 4, SEQ ID NO: 12 or SEQ ID NO: 16, ii) and a test compound; b) contacting said first and second groups of cells with said compound; and c) detecting the effects of said compound. This method may also be used with mutated sequences. In still another embodiment, a second group of cells comprise a recombinant expression vector, wherein said vector comprises a suitable control (e.g., an empty vector).

The present invention also contemplates a method of screening for homologs, said method comprising: a) providing in any order: i) a nucleic acid comprising at least a portion of the sequence of SEQ ID NO:1, and ii) DNA libraries from cells or tissues suspected to comprise said homolog; and b) hybridizing said portion of the sequence of SEQ ID NO:1 with said DNA of said library under conditions such that said DNA suspected of coding for said homolog is detected. This method may also be used with SEQ ID NOS: 4, 12 and 16. In one embodiment, the present invention contemplates that said hybridization will be, for example, under conditions of low stringency, as discussed below. In another embodiment, the present invention contemplates that said hybridization will be under conditions of high stringency, as discussed below.

The present invention also contemplates a method of screening for interactive peptides, said method comprising: a) providing in any order: i) a peptide comprising at least a portion of the peptide sequence of SEQ ID NO: 2 (including but not limited to portions that are part of fusion proteins, e.g., proteins that contain another portion, such as a portion useful for protein purification) and b) an extract from a source (e.g., cells or tissues) suspected of containing or comprising said interactive peptides; and c) mixing said peptide with said extract under conditions such that said interactive peptide is detected. This method may also be used with at least a portion of the peptide sequences of SEQ ID NOS: 3 and 5 and translation products of SEQ ID NO: 12.

The present invention also contemplates an approach for screening for interactive peptides, said method comprising: a) providing in any order: i) antibodies reactive with (e.g., specific for) at least a portion of a peptide having the sequence of SEQ ID NO: 2, and ii) an extract from a source (e.g. cells or tissues) suspected of having said interactive peptide(s); and b) mixing said antibody with said extract under conditions such that said interactive peptide is detected. This method may also be used with antibodies reactive with at least a portion of the peptide sequences of SEQ ID NOS: 3 and 5 and translation products of SEQ ID NO: 12.

The present invention contemplates the generation of cell lines that express ferret coronavirus nucleotide sequences such as, for example, the nucleotide sequence encoding the spike peptide, the nucleotide sequence encoding the M and N region peptide and the nucleotide sequence encoding the pol region peptide or portions thereof. The present invention is not limited to any particular cell line.

The present invention contemplates DNA binding assays where a) ferret coronavirus nucleotide sequences (e.g., SEQ ID NO: 1, SEQ ID NO: 4, SEQ ID NO: 12 and SEQ ID NO: 16), or portions thereof, is either i) adhered to a solid support surface or ii) placed in a suspension, b) compounds suspected of binding to the DNA are added in a manner that promotes binding and c) binding is measured. Detection methods utilized include, but are not limited to, staining, gel electrophoresis and spectrophometric methods.

The present invention contemplates high throughput screening methods. Such methods include, but are not limited to, DNA array assays, spectrophotometric assays, mass spectrometry, the use of robotics, the use of computerized assay systems and the use of commercially available systems.

The present invention contemplates screening for proteins that bind to ferret coronavirus binding sites. The present invention is not limited to any particular assay method. In one embodiment, DNA encoding the sequences of the present invention (proteins encoded by SEQ ID NOS: 1, 4, 12 and 16 or portions thereof) are attached to a solid surface (e.g., a microchip) and protein suspected of binding the DNA sequences are placed in contact with the DNA. Attached proteins are then analyzed by methods know to those in the art.

The present invention contemplates a method, comprising: a) providing in any order: i) a first solid support comprising nucleic acid from a DNA library of the species to be examined and ii) an oligonucleotide, selected form a group consisting of SEQ ID NOS: 1, 4, 12 and 16 and portions thereof, b) contacting said solid support with said oligonucleotide under conditions such that hybridization takes place. In one embodiment, the present invention contemplates the solid support is a microchip.

The present invention contemplates a method of screening a compound, said method comprising: a) providing in any order: i) a first group of cells comprising a recombinant expression vector, wherein said vector comprises at least a portion of the an oligonucleotide, selected form a group consisting of SEQ ID NOS: 1, 4, 12 and 16 and portions thereof, ii) a second group of cells comprising a recombinant expression vector, wherein said vector comprises an empty vector, and iii) a test compound; b) contacting said first and second groups of cells with said compound to produce a detectable reaction product; and c) culturing said cells under conditions such that said detectable reaction product is detected.

The present invention contemplates a method of screening for homologs, said method comprising: a) providing in any order: i) a nucleic acid comprising at least a portion of an oligonucleotide, selected form a group consisting of SEQ ID NOS: 1, 4, 12 and 16 and portions thereof, and ii) DNA libraries from cells or tissues suspected to comprise said homolog; and b) hybridizing said first or second nucleic acid with said DNA of said library under conditions such that said DNA suspected of coding for said homolog is detected.

The present invention contemplates a method comprising: a) providing in any order: i) a peptide comprising at least a portion of the peptide selected form a group consisting of sequence of SEQ ID NOS: 2, 3, 5 and 17 and translation products of SEQ ID NO: 12 and ii) an extract from source suspected of having one or more interactive peptides; and c) mixing said peptide with said extract under conditions such that said one or more interactive peptides is detected. In one embodiment, the peptide is a fusion protein.

The present invention contemplates a method comprising: a) providing in any order: i) antibodies reactive with at least a portion of a peptide having the sequence of at least a portion of the peptide selected form a group consisting of sequence of SEQ ID NO: 2, 3, 5 and 17 and translation products of SEQ ID NO: 12, and ii) an extract from a source suspected of having one or more interactive peptides; and b) mixing said antibody with said extract under conditions such that said one or more interactive peptides is detected. In one embodiment, the peptide is a fusion protein.

In one embodiment, the present invention contemplates a purified oligonucleotide selected from the group consisting of SEQ ID NOS: 1, 4, 12 and 16 or a portion thereof. In another embodiment, the present invention contemplates a purified oligonucleotide selected from the group consisting of SEQ ID NOS: 1, 4, 12 and 16 wherein, said oligonucleotide has at least 90% homology to said sequence.

In one embodiment, the present invention contemplates a purified peptide selected from the group consisting of SEQ ID NOS: 2, 3, 5 and 17 and translation products of SEQ ID NO: 12 or a portion thereof. In another embodiment, the present invention contemplates a purified peptide selected from the group consisting of SEQ ID NOS: 2, 3, 5 and 17 wherein, said peptide has at least 90% homology to said sequence. In yet another embodiment, the present invention contemplates an antibody capable of binding to at least a portion of the translation product of SEQ ID NOS: 1, 4, 12 and 16.

In one embodiment, the present invention contemplates a method comprising:

a) providing fecal matter from a subject; and b) detecting the presence or absence of a nucleotide sequence that has at least 90% homology to SEQ ID NOS: 1, 4, 12 and 16 or portion thereof. In another embodiment, the present invention contemplates that detecting of presence or absence of a nucleotide sequence that has at least 90% homology to SEQ ID NOS: 1, 4, 12 and 16 is accomplished by hybridization analysis.

In one embodiment, the present invention contemplates a method comprising: a) providing fecal matter from a subject; and b) detecting the presence or absence of a peptide sequence that has at least 90% homology to SEQ ID NOS: 2, 3, 5 and 17 and translation products of SEQ ID NO: 12, or portion thereof. In another embodiment, the present invention contemplates that detecting of presence or absence of a nucleotide sequence that has at least 90% homology to SEQ ID NOS: 1, 4, 12 and 16 is accomplished by an antibody assay.

In one embodiment, the present invention contemplates a kit for determining if a subject is infected with ferret coronavirus comprising a detection assay, wherein the detection assay is capable of specifically detecting a peptide sequence that has at least 90% homology to SEQ ID NOS: 2, 3, 5 and 17 and translation products of SEQ ID NO: 12, or portion thereof. In another embodiment, the present invention contemplates a kit for determining if a subject is infected with ferret coronavirus comprising a detection assay, wherein the detection assay is capable of specifically detecting a peptide sequence that has at least 90% homology to SEQ ID NOS: 1, 4, 12 and 16 or portion thereof. In yet another embodiment, the present invention contemplates a kit of wherein the detection assay comprises a nucleic acid probe that hybridizes under stringent conditions to a nucleic acid sequence comprising at least 90% homology to SEQ ID NOS: 1, 4, 12 and 16 or portion thereof. In yet still another embodiment, the present invention contemplates that detecting of presence or absence of a nucleotide sequence that has at least 90% homology to SEQ ID NOS: 1, 4, 12 and 16 is accomplished by hybridization analysis. In yet still another embodiment, the present invention contemplates a kit of, wherein the detection assay comprises an antibody capable of specifically detecting a peptide sequence that has at least 90% homology to SEQ ID NOS: 2, 3, 5 and 17 and translation products of SEQ ID NO: 12, or portion thereof. Additionally, in yet another embodiment, the present invention contemplates a PCR-based kit comprising the sequences of the preset invention.

In one embodiment, the present invention contemplates a computer readable medium encoding a representation of the nucleic acid sequence of SEQ ID NOS: 1, 4, 12 and 16. In one embodiment, the present invention contemplates a computer readable medium encoding a representation of the amino acid sequence of SEQ ID NOS: 2, 3, 5 and 17 and translation products of SEQ ID NO: 12.

In one embodiment, the present invention contemplates a method of treating a subject with symptoms of ECE, comprising administering a therapeutically effective amount of an antibody capable of binding at least a portion of SEQ ID NOS: 2, 3, 5 and 17 and translation products of SEQ ID NO: 12 such that the symptoms of the disease are reduced.

In one embodiment, the present invention contemplates a method, comprising: a) providing, i) peptide sequences selected from a group consisting of SEQ ID NOS: 2, 3, 5 and 17 and translation products of SEQ ID NO: 12, or portion thereof, bound to a solid substrate, ii) a compound and, iii) a detection means; b) contacting said compound to said peptides to produce a peptide-compound complex; c) detecting said peptide-compound complex with said detection means. In another method, the present invention contemplates a method, comprising: a) providing, i) a compound attached to a solid substrate, ii) peptide sequences selected from a group consisting of SEQ ID NOS: 2, 3, 5 and 17 and translation products of SEQ ID NO: 12, or portion thereof and, iii) a detection means; b) contacting said peptides to said compound to produce a peptide-compound complex; c) detecting said peptide-compound complex with said detection means. In another embodiment, the method utilizes a detection means comprising antibodies. In yet another embodiment, the method comprises antibodies that are fluorescently labeled.

The present invention contemplates variants of the peptides (SEQ ID NOS: 2, 3, 5 and 17 and translation products of SEQ ID NO: 12) based on conservative substitution rules. For example, the underlined amino acids in FIG. 3 are exemplary amino acids for conservative substitution.

The present invention contemplates the production and use of a vaccine for the preventive treatment of ECE. In one embodiment, killed ferret coronavirus is used as an immunogen. The isolation of ferret virus is taught in Example 3. Ferret coronavirus may be killed, for example, by heat or detergent. In another embodiment, the peptides of the present invention (e.g., SEQ ID NOS: 2, 3, 5 and 17 and translation products of SEQ ID NO: 12) are used as immunogens. In yet another embodiment, known adjuvants (e.g., KLH, CT, etc.) are added to the killed ferret coronavirus or peptide of the present invention to increase immunogenicity.

In other embodiments, the present invention contemplates other methods making vaccines composed of one or more ECE-specific polypeptides for the preventive treatment of ECE. Various embodiments include, but are not limited to, whole virion modified-live virus (generated, for example, by repeated in vivo or in vitro passage), DNA vaccine delivered by existing approaches (intermuscular, subcutaneous, recombinant vaccines (for example, vaccinia, canarypox, fowlpox, adenovirus [E1 and/or E3 deleted] Herpesvirus [TK deleted or deletion in one or more non-essential glycoprotein encoding genes], vesicular stomatitis virus, venezuelan equine encephalitis, semliki forest virus, polio virus vector, baculovirus, *salmonella typhimurium, shigella* and BCG), ISCOM-based subunit, monomeric or polymeric synthetic peptide(s) with or without adjuvants, virosomes, BACVAC, virus-like particle (VLP) vaccine composed of one or more ECE-specific polypeptides generated in the baculovirus expression system, temperature sensitive mutants, cold-adaptive mutants, infectious clone based vaccine and all currently existing approaches to mucosal vaccination (for example, micro- and nanoparticles, mucoadhesive microspheres, liposomes, bacterial enterotoxins as mucosal adjuvant proteosomes, bacterial outer membrane proteins, VLP vaccine format, admixture of excipients such as Polysorbate 20 or Cremophor EL, Quil A adjuvant, prime-boost approach, plant lectins, gastrointestinal lamina propria targeting, Peyer's patch targeting, etc.). All of these approaches are known to those practiced in the art. In another embodiment, modification of cytokine production by dendritic cells via transfection or genetic engineering intestinal dendritic cells (possibly with cytokine gene co-expression) may be used as a preventative treatment of ECE.

In one embodiment, the present invention contemplates a diagnostic test for ECE. The present invention is not limited to any particular diagnostic test. Many diagnostic tests are contemplated. For example, in one embodiment the present invention contemplates a diagnostic test comprising a fluorescent antibody assay comprising a monoclonal or polyclonal antibody that is specific for at least one ferret coronavirus peptide or mutated ferret coronavirus peptide specific. In another embodiment, the present invention contemplates a diagnostic test comprising immunohistochemistry with ferret coronavirus peptide specific monoclonal or polyclonal antibodies. Although the present invention is not limited to any particular type of immunohistochemical diagnostic test, one example is an ELISA assay. In another embodiment, the present invention contemplates diagnostic tests that comprise the reverse transcription polymerase chain reaction (RT-PCR). Although the present invention is not limited to any particular type of RT-PCR assay, examples are RT-PCR with ferret coronavirus specific primers, real time RT-PCR in all of the existing formats with ferret coronavirus-specific primers and probe sequences, multiplex RT-PCR to simultaneously detect ferret coronavirus). In another embodiment, the present invention contemplates a diagnostic test comprising antigen detection ELISA with at least one expressed ferret coronavirus peptide or mutated peptide-specific antibodies as capture and/or detection antibodies. All of these approaches are known to those practiced in the art.

In one embodiment, the present invention contemplates a purified oligonucleotide having a nucleic acid sequence selected from the group consisting of SEQ ID NOS: 1, 4, 12 and 16 or a portion thereof. In another embodiment, the present invention contemplates the oligonucleotide a purified oligonucleotide having a nucleic acid sequence selected from the group consisting of SEQ ID NOS: 1, 4, 12 and 16 or a portion thereof, wherein the sequence is operably linked to a heterologous promoter.

In one embodiment, the present invention contemplates a vector comprising the oligonucleotide of SEQ ID NOS: 1, 4, 12 and 16 or a portion thereof. In another embodiment, the present invention contemplates a host cell comprising the vector of a vector comprising the oligonucleotide of SEQ ID NOS: 1, 4, 12 and 16 or a portion thereof. In yet another embodiment, the present invention contemplates that the host cell is selected from the group consisting of animal and plant cells. In still yet another embodiment, the present invention contemplates that the host cell is located in an organism.

In one embodiment, the present invention contemplates a computer readable medium encoding a representation of the nucleic acid sequence of the oligonucleotide of SEQ ID NOS: 1, 4, 12 and 16 or a portion thereof.

In one embodiment, the present invention contemplates an oligonucleotide probe capable of hybridizing to a portion of the oligonucleotide of SEQ ID NOS: 1, 4, 12 and 16 or a portion thereof. In yet another embodiment, the present invention contemplates that the oligonucleotide probe is labeled.

In one embodiment, the present invention contemplates a purified peptide having an amino acid sequence selected from the group consisting of SEQ ID NOS: 2, 3, 5 and 17 and translation products of SEQ ID NO: 12 or a portion thereof. In another embodiment, the present invention SEQ ID NOS: 2, 3, 5 and 17 and translation products of SEQ ID NO: 12 or a portion thereof. In yet another embodiment, the present invention contemplates a computer readable medium encoding a representation of the polypeptides of SEQ ID NOS: 2, 3, 5 and 17 and translation products of SEQ ID NO: 12 or a portion thereof.

In one embodiment, the present invention contemplates a method comprising: a) providing fecal matter from a subject; and b) detecting the presence or absence of a nucleotide sequence that has at least 90% homology to SEQ ID NOS: 1, 4, 12 and 16, or portion thereof. In another embodiment, the present invention contemplates the methods wherein the detecting is accomplished by hybridization analysis.

In one embodiment, the present invention contemplates a method comprising: a) providing fecal matter from a subject; and b) detecting the presence or absence of a peptide sequence that has at least 90% homology to SEQ ID NOS: 2, 3, 5 and 17 and translation products of SEQ ID NO: 12, or portion thereof. In another embodiment, the present invention contemplates the methods wherein the detecting is accomplished by an antibody assay.

In one embodiment, the present invention contemplates a kit for determining if a subject is infected with ferret coronavirus comprising a detection assay, wherein the detection assay is capable of specifically detecting a peptide sequence that has at least 90% homology to SEQ ID NOS: 2, 3, 5 and 17 and translation products of SEQ ID NO: 12, or portions thereof.

In one embodiment, the present invention contemplates a kit for determining if a subject is infected with ferret coronavirus comprising a detection assay, wherein the detection assay is capable of specifically detecting a peptide sequence that has at least 90% homology to SEQ ID NOS: 1, 4 12 and 16, or portions thereof. In another embodiment, the present invention contemplates the above kit, wherein the detection assay comprises a nucleic acid probe that hybridizes under stringent conditions to a nucleic acid sequence comprising at least 90% homology to SEQ ID NOS: 1, 4 and 12, or portions thereof. In yet another embodiment, the present invention contemplates the above method, wherein the detecting is accomplished by hybridization analysis. In still yet another embodiment, the present invention contemplates the kit, wherein the detection assay comprises an antibody capable of specifically detecting a peptide sequence that has at least 90% homology to SEQ ID NOS: 2, 3, 5 and 17 and translation products of SEQ ID NO: 12, or portions thereof.

In one embodiment, the present invention contemplates a purified oligonucleotide having a nucleic acid sequence selected from the group consisting of SEQ ID NOS: 1, 4, 12 and 16 or a portion thereof. The portions (or fragments), as defined below, may range in size from ten nucleotide residues to the entire nucleotide sequence minus one nucleotide. In one embodiment, said portion is between 10 and 100 nucleotide residues. In a preferred embodiment, the portion is between 10 and 30 nucleotide residues. Such portions may be utilized as probes. In another embodiment, the present invention contemplates that the purified oligonucleotide of is operably linked to a heterologous promoter. In yet another embodiment, the present invention contemplates a vector comprising the purified oligonucleotide. In still yet another embodiment, the present invention contemplates a host cell comprising said vector. In yet another embodiment, the present invention contemplates said host cell, wherein the host cell is selected from the group consisting of animal and plant cells. In yet another embodiment, the present invention contemplates said host cell, wherein the host cell is located in an organism.

In one embodiment, the present invention contemplates a computer readable medium encoding a representation of the nucleic acid sequences SEQ ID NOS: 1, 4, 12 and 16.

In one embodiment, the present invention contemplates an oligonucleotide probe capable of hybridizing to a portion of the oligonucleotides of SEQ ID NOS: 1, 4, 12 and 16. In one embodiment, the present invention contemplates that said hybridization will be, for example, under conditions of low stringency, as discussed below. In another embodiment, the present invention contemplates that said hybridization will be under conditions of high stringency, as discussed below. In another embodiment, the present invention contemplates that the oligonucleotide probe is labeled.

In one embodiment, the present invention contemplates a purified peptide having an amino acid sequence selected from the group consisting of SEQ ID NOS: 2, 3, 5 and 17 or a portion thereof. The portions (or fragments), as defined below, may range in size from four amino acids to the entire amino acid sequence minus one amino acid. In one embodiment, said portion is between 4 and 50 amino acids. In a preferred embodiment, the portion is between 10 and 15 amino acids. Such portions may be utilized as antigens or ligands. In another embodiment, the present invention contemplates an antibody capable of binding to a portion of said peptide. In yet another embodiment, the present invention contemplates a computer readable medium encoding a representation of said polypeptides. In still yet another embodiment, the present invention contemplates a purified peptide translated from an open reading frame of nucleotide SEQ ID NO: 12 or a portion thereof. In still yet another embodiment, the present invention contemplates an antibody capable of binding to a portion said peptide.

DESCRIPTION OF THE DRAWINGS

FIG. 1 shows the nucleotide sequences of the ferret coronavirus encoding the M and N region peptide (SEQ ID NO:1) and the spike (SEQ ID NO:4).

FIG. 2 shows the peptide sequences of the ferret coronavirus M and N region peptide (SEQ ID NOS:2 and 3) and the spike (SEQ ID NO:5).

FIG. 3 shows SEQ ID NOS: 2, 3 and 5. By way of illustration, the underlined amino acids are candidates for substitution and for the production of peptide variants. In one embodiment, each variant comprises a single amino acid substitution. In another embodiment, each variant comprises more than one amino acid substitution. In yet another embodiment, any amino acid may be used as a substitute for the production of peptide variants.

FIG. 4 shows the nucleotide sequence encoding the ferret coronavirus pol region peptide (SEQ ID NO: 12).

FIG. 5 shows the nucleotide sequence of the reverse complement of the ferret coronavirus spike peptide (VA strain) (SEQ ID NO: 15).

FIG. 6 shows the 3' end of M, entire N (capsid gene) region (ATG start codon emboldened and underlined; TAA stop codon emboldened and underlined), plus the remaining 3' terminus of Ferret Enteric Coronavirus (FECV) genomic sequence (SEQ ID NO: 16).

FIG. 7 shows the FECV capsid protein amino acid sequence (SEQ ID NO: 17).

DEFINITIONS

In order to Better Understand the Invention, the Following Definitions are Provided.

The terms "protein," "peptide" and "polypeptide" refer to compounds comprising amino acids joined via peptide bonds and these terms are used interchangeably. A "protein," "peptide" or "polypeptide" encoded by a gene is not limited to the amino acid sequence encoded by the gene, but includes post-translational modifications of the protein. A "protein," "peptide" or "polypeptide" will also refer to a region or fragment of the named peptide.

Where the term "amino acid sequence" is recited herein to refer to an amino acid sequence of a protein molecule, "amino acid sequence" and like terms, such as "polypeptide," "peptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid. The term "portion" when used in reference to a nucleotide sequence (as in "a portion of a given nucleotide sequence") refers to fragments of that nucleotide sequence. The fragments may range in size from ten nucleotide residues to the entire nucleotide sequence minus one nucleotide. Such fragments may be utilized as probes.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

FIG. 3 shows (by way of illustration) a peptides of the present invention with the exemplary substitutable amino acids underlined. The present invention contemplates variants where one or more of the underlined amino acids are substituted with an amino acid selected from the respective group with another from the same group as illustrated: valine-leucine-isoleucine, phenylalanine-tyrosine, lysine-arginine, alanine-valine, and asparagine-glutamine. These examples are only illustrative and are do not limit the present invention in anyway.

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations.

The term "gene" refers to a nucleic acid (e.g., DNA sequence, RNA sequence or nucleotide sequence) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. A "translation product" of a DNA sequence is the peptide sequence generated via from the mRNA encoded by the DNA.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

In particular, the term "coronavirus spike protein gene", or equivalent, refers to a M and N region nucleotide sequence (e.g., as shown in SEQ ID NO:1). However, it is also intended that the term encompass fragments of the M and N region sequence, as well as other domains with the full-length M and N region nucleotide sequence. Furthermore, the terms "M and N region nucleotide sequence" or "M and N region polynucleotide sequence" encompasses DNA, cDNA, and RNA (e.g., mRNA) sequences. Likewise, the term "coronavirus protein gene" refers to any nucleotide sequence comprising the ferret coronavirus genome. Furthermore, the term "coronavirus spike gene", or equivalent, refers to a spike nucleotide sequence (e.g., as shown in SEQ ID NO:4). However, it is also intended that the term encompass fragments of the spike sequence, as well as other domains with the full-length spike nucleotide sequence. Furthermore, the terms "spike nucleotide sequence" or "spike polynucleotide sequence" encompasses DNA, cDNA, and RNA (e.g., mRNA) sequences. Likewise, the term "coronavirus protein gene" refers to any nucleotide sequence comprising the ferret coronavirus genome.

The term "heterologous" when used in reference to a gene refers to a gene encoding a peptide that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise gene sequences that comprise cDNA forms of a gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (e.g., genes expressed in loci where the gene is not normally expressed).

The term "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The terms "oligonucleotide" or "polynucleotide" or "nucleotide sequence" or "nucleic acid sequence" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total"

complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term, "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*U.S.A.*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4(H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4(H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4(H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

The term "polymorphic locus" refers to a genetic locus present in a population that shows variation between members of the population (i.e., the most common allele has a frequency of less than 0.95). Thus, "polymorphism" refers to the existence of a character in two or more variant forms in a population. A "single nucleotide polymorphism" (or SNP) refers a genetic locus of a single base which may be occupied by one of at least two different nucleotides. In contrast, a "monomorphic locus" refers to a genetic locus at which little or no variations are seen between members of the population (generally taken to be a locus at which the most common allele exceeds a frequency of 0.95 in the gene pool of the population).

A "frameshift mutation" refers to a mutation in a nucleotide sequence, usually resulting from insertion or deletion of a single nucleotide (or two or four nucleotides) which results in a change in the correct reading frame of a structural DNA sequence encoding a protein. The altered reading frame usually results in the translated amino-acid sequence being changed or truncated.

A "splice mutation" refers to any mutation that affects gene expression by affecting correct RNA splicing. Splicing mutation may be due to mutations at intron-exon boundaries which alter splice sites.

The term "detection assay" refers to an assay for detecting the presence or absence of a sequence or a variant nucleic acid sequence (e.g., mutation or polymorphism in a given allele of a particular gene, e.g., ferret coronavirus spike gene), or for detecting the presence or absence of a particular protein (e.g., ferret coronavirus spike peptide) or the structure or activity or effect of a particular protein or for detecting the presence or absence of a variant of a particular protein.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q_ replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlain et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length.

Promoters may be tissue specific or cell specific. The term "tissue specific" as it applies to a promoter refers to a promoter that is capable of directing selective expression of a nucleotide sequence of interest to a specific type of tissue in the relative absence of expression of the same nucleotide sequence of interest in a different type of tissue. Tissue specificity of a promoter may be evaluated by, for example, operably linking a reporter gene to the promoter sequence to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or inducible. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, an "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual,* 2nd ed., Cold Spring Harbor Laboratory Press, New York [1989] pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6-16.7).

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "stable expression" means the expression of an exogenous sequence wherein the transfected sequences has been integrated into the genome.

The term "transient expression" means the expression of an exogenous sequence wherein the transfected sequences has failed to integrate into the genome.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "transgene" refers to a foreign gene that is placed into an organism by the process of transfection. The term "foreign gene" refers to any nucleic acid (e.g., gene sequence) that is introduced into the genome of an organism by experimental manipulations and may include gene sequences found in that organism so long as the introduced gene does not reside in the same location as does the naturally-occurring gene.

The term "transgenic" when used in reference to a host cell or an organism refers to a host cell or an organism that contains at least one heterologous or foreign gene in the host cell or in one or more of cells of the organism.

The term "host cell" refers to any cell capable of replicating and/or transcribing and/or translating a heterologous gene. Thus, a "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos.,6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. [1989] *Molecular Cloning: A Laboratory Manual,* Cold Spring Harbor Press, NY, pp 9.31-9.58).

The term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. [1989] supra, pp 7.39-7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "antigenic determinant" refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 96% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution. Compositions comprising polynucleotide sequences encoding coronavirus spike peptide (e.g., SEQ ID NO: 4) and M and N region peptide (e.g., SEQ ID NO: 1) or fragments thereof may be employed as hybridization probes. In this case, the ferret coronavirus encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials) to be effective in such treatment or prevention.

As used herein, the term "response," when used in reference to an assay, refers to the generation of a detectable signal (e.g., accumulation of reporter protein, increase in ion concentration, accumulation of a detectable chemical product).

The terms "sample" and "source" are used in their broadest sense. In one sense they can refer to a animal cell or tissue. In another sense, they is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

The term "immunohistochemical assay" is defined as an assay that comprises peptides (e.g., antibodies) that recognized antigenic determinants (e.g., epitopes). The peptides are linked either directly or indirectly to other peptides or other compounds (e.g., fluorescent peptides or chemicals, enzymes and the like) that give a detectable signal in the given assay system. An example of an immunohistochemical assay would be an ELISA assay.

GENERAL DESCRIPTION OF THE INVENTION

Disease Etiology

Epizootic catarrhal enteritis in ferrets is characterized by outbreaks of green mucoid diarrhea and microscopic findings of lymphocytic enteritis accompanied by villus atrophy, fusion, and blunting and vacuolar degeneration or necrosis of the apical epithelium. The pathogenesis and clinical progression of this condition is similar to enteritis caused by coronaviruses in other species. Infected ferrets often have lethargy and anorexia as initial clinical signs that are evident within 48 to 72 hours after exposure. Vomiting, if present, is the first sign of gastrointestinal tract disease in most ferrets. It often subsides within hours, and a characteristic profuse green watery-to-mucoid diarrhea ensues. The mucoid nature of the feces in the early stages of this disease is a characteristic finding in ECE and has been described in enteric coronavirus infections in other species. In addition to the characteristic gross and microscopic lesions detected in the study reported here, mesenteric lymph nodes are often enlarged, with moderate to substantial paracortical and follicular hyperplasia being a prominent microscopic finding.

The hypersecretory phase of uncomplicated ECE often resolves within 5 to 7 days in healthy young ferrets, and a subsequent period of maldigestion or malabsorption of widely varying duration may develop. During the malabsorptive phase of the disease, feces have a characteristic grainy appearance attributable to undigested fats and proteins. Microscopic examination of feces may reveal undigested fat droplets or starch granules but is unreliable, because results are insensitive, imprecise, and may be complicated by increased gastrointestinal transit time in affected ferrets and variable diet composition. Microscopic lesions in jejunal biopsy specimens during this time consist of a combination of villus shortening and widespread lymphocytic enteritis characterized by prominent increases in numbers of intraepithelial lymphocytes and total numbers of lymphocytes within the intestinal submucosa and lymphoid follicles.

Clinicopathologic findings are generally nonspecific and attributable to substantial dehydration and inanition in acutely affected ferrets. Inanition causes increased serum activity of alanine amino transferase and alkaline phosphatase attributable to mobilization of peripheral fat stores to the liver, with resultant hepatocellular swelling. Leukocytosis may develop in ferrets with concurrent bacterial infections or gastric ulceration. Mild hypoalbuminernia may be the result of a combination of enteritis and malabsorption in chronically affected ferrets. Definitive diagnosis in ferrets with equivocal clinical histories may be accomplished by microscopic examination of intestinal biopsy or necropsy specimens that have characteristic lesions (Williams, B. H., et al., "Epizootic Caterrhal Enteritis: a Novel Diarrheal Disease in the Ferret (*Mustela putoriusfuro*)," in *Proceedings, 8th Annu. Small Mammal Conf.,* Baltimore, Md., 1997).

Transmission and epidemiologic features of ECE in naive ferret populations are similar to enteric coronaviral infections in other animal species, particularly epizootic catarrhal gastroenteritis in mink. Features include low morbidity in kits (new born to young ferrets), high transmissibility, and a mortality rate of about 5% unless infection is complicated with concurrent bacterial infections or other diseases in which case the death rate is higher. Older ferrets with concurrent diseases such as insulinoma, adrenal-associated endocrinopathy, and long-standing gastric infection with *Helicobacter mustelae* often have more severe clinical signs and higher mortality than younger ferrets. Concurrent bacterial infections have been recognized as an associated risk factor for increased mortality in coronaviral infections. Early outbreaks of disease similar to ECE developed immediately after ferret shows in which large numbers of ferrets were congregated, and transmission of virus by contaminated handlers could occur.

Disease Diagnosis

Because of the inherent difficulty of propagating coronaviruses in vitro, definitive diagnosis of coronavirus infection in animals is difficult and often frustrating. In acute phases of disease, coronavirus-like particles may be identified by electron microscopic examination of feces but this method of diagnosis is not practical for everyday usage. The term "coronavirus-like particle" is used to describe pleomorphic particles ranging in size from 60 to 220 nm with morphology consistent with coronavirus particles, when results of other tests are negative or unavailable. In chronic stages of the disease, virions may still be intermittently shed in the feces; however, their concentration may be below that necessary for identification.

General Characteristics of Coronaviruses

Coronaviruses are pleomorphic single-stranded RNA viruses that affect numerous animal species. In several species, including dogs, cats, pigs, cattle, rabbits, mice, rats, poultry and, possibly, humans, coronaviruses are responsible for enteric infection, diarrhea and, in some species, wasting and death. The Coronavirus genus contains 4 antigenic groups that contain several species and serotypes. The strong immunoreactivity identified with the monoclonal antibodies used in the Example 3 suggests that this particular coronavirus belongs to Coronavirus antigenic group 1, a mammalian group containing the coronaviruses that cause transmissible gastroenteritis in pigs, feline infectious peritonitis in cats and enteritis in dogs.

DETAILED DESCRIPTION OF THE PREFERRED EMBODIMENTS

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references [See, generally, Sambrook, et al., Molecular Cloning: A Laboratory Manual, 3d ed. (2001) Cold Spring Harbor Laboratory Press, Cold Spring Harbor, N.Y., and Current Protocols in Molecular Biology (1996) John Wiley and Sons, Inc., N.Y.].

Oligonucleotides can be synthesized on an Applied BioSystems oligonucleotide synthesizer [for details see Sinha et al., Nucleic Acids Res. 12:4539 (1984)], according to specifications provided by the manufacturer. Complementary oligonucleotides are annealed by heating them to 90° C. in a solution of 10 mM Tris-HCl buffer (pH 8.0) containing NaCl (200 mM) and then allowing them to cool slowly to room temperature. For binding and turnover assays, duplex DNA is purified from native polyacrylamide (15% w/v) gels. The band corresponding to double-stranded DNA is excised and soaked overnight in 0.30 M sodium acetate buffer (pH 5.0) containing EDTA (1 mM). After soaking, the supernatant is extracted with phenol/chloroform (1/1 v/v) and precipitated with ethanol. DNA substrates are radiolabeled on their 5'-OH group by treatment with [g-$^{32}$P]ATP and T4 polynucleotide kinase. Salts and unincorporated nucleotides are removed by chromatography on Sephadex G columns.

The present invention contemplates assays for detecting the ability of agents to inhibit or enhance ferret coronavirus function, ferret coronavirus spike peptide function, ferret coronavirus pol peptide function and ferret coronavirus M and N region peptide function where high-throughput screening formats are employed together with large agent banks (e.g., compound libraries, peptide libraries, and the like) to identify such antagonists or agonists and binding partners. Such ferret coronavirus function, ferret coronavirus spike peptide, ferret coronavirus pol peptide function and ferret coronavirus M and N region peptide antagonists and agonists and binding partners may be further developed as potential therapeutics and diagnostic or prognostic tools for ferret ECE.

In embodiments of the present invention, ferret coronavirus nucleotide sequences including the spike peptide nucleotide sequences, pol peptide nucleotide sequences and M and N region peptide nucleotide sequences, and derivative products of the nucleotide sequences such as peptides, peptide fragments, antibodies, expression vectors and transgeneic animals, are useful for the diagnosis and treatment of ferret ECE.

In other preferred embodiments, ferret coronavirus function and ferret coronavirus spike peptide nucleotide sequence, pol peptide nucleotide sequence and M and N region peptide nucleotide sequence and associated peptides or fragments thereof, can be used in an in vitro cell system for identifying other similar inhibitors peptides such as homologs. Also, the ferret coronavirus function and ferret coronavirus spike peptide fragments, pol peptide fragments and M and N region peptide fragments can be used to screen for peptides or other compounds that bind ferret coronavirus function and ferret coronavirus spike peptides.

In yet other preferred embodiments, the spike peptide nucleotide sequence, pol peptide nucleotide sequence and M and N region peptide nucleotide sequence, and associated peptides or fragments thereof, can be used in the development of screening assays for the identification of ferrets with ferret coronavirus. Such assays, which are an improvement over traditional methods of diagnosis, will make the diagnosis of this disease easy and accurate.

Diagnostic Assays and other Uses of the Invention

In preferred embodiments, the present invention provides the DNA encoding the ferret coronavirus, especially the spike protein, pol protein and the M and N region of the ferret coronavirus. Although the present invention is not limited to any particular mechanism, the coronavirus is believed to be the causative agent of ferret ECE.

In other embodiments, the invention provides nucleotide sequences encoding the coronavirus spike polypeptide and spike peptide portions, the coronavirus pol polypeptide and pol peptide portions, as well as the coronavirus M and N polypeptide and M and N region portions, as part of expression vectors for introduction into cells. The invention provides methods of identifying intracellular or extracellular molecules which interact with ferret coronavirus, spike peptide, pol region peptide and M and N region peptide or ferret coronavirus, spike peptide fragments, pol peptide fragments and M and N region peptide, as well as exogenous agents (i.e., drugs) which disrupt the binding of ferret coronavirus and spike, pol and M and N region peptide and/or fragments thereof to such intracellular or extracellular targets.

In one embodiment, it is contemplated that the claimed polypeptide ferret coronavirus and spike peptide and ferret coronavirus and spike peptide fragments thereof, find particular use in screening assays for agents or lead compounds for agents useful in the diagnosis, prognosis or treatment of ECE and related diseases. One such assay involves forming mixtures of 1) ferret coronavirus and spike peptide (or fragments thereof) and 2) a spike peptide- or coronavirus-binding substrate, in the presence or absence of 3) a prospective drug candidate. The mixtures are made under conditions that permit the binding of the spike peptide- or coronavirus-binding substrate to the spike peptide of ferret coronavirus (or fragments thereof) and the mixtures are then analyzed for the presence of such binding. A difference in such binding in the presence of such a drug candidate indicates that the agent is capable of modulating the binding of the spike peptide or coronavirus (or fragments thereof) to an spike peptide- or coronavirus-binding substrate. The assays of the present invention provide for facile high-throughput screening of compounds suspected to be able to inhibit such binding (e.g., compound libraries, peptide libraries, and the like) to identify potential drug candidates. Additionally, the present invention contemplates the foregoing embodiment wherein, the peptide used comprises the pol region peptide, the M and N region peptide, or portions thereof.

Coronavirus, spike peptide, pol region peptide and M and N region peptide (and Coronavirus, spike peptide, pol region peptide and M and N region peptide mutants) screening methods, including cell-free methods and cellular methods, can be used in certain embodiments in the practice of this invention. Cellular screening methods within the scope of this invention can involve transient expression vectors or stable transformation. Various ferret coronavirus, spike peptide, pol region peptide and M and N region peptide and ferret coronavirus, spike peptide, pol region peptide and M and N region peptide mutant screening protocols can be designed, according to well-known principles, by one of ordinary skill in the art. Soluble forms of coronavirus, spike peptide, pol region peptide and M and N region peptide and coronavirus, spike peptide, pol peptide and M and N region peptide interaction partners can be utilized in cell free coronavirus and spike peptide inhibitor screening protocols.

Preferably, coronavirus, spike peptide, pol peptide and M and N region peptide inhibitor screening is carried out in a cellular system, using a reporter strain of cultured mammalian cells, transformed with one or more vectors encoding ferret coronavirus, spike peptide, pol region peptide and M and N region peptide and other assay components, as necessary.

Preferably, a spike-encoding sequence, pol-encoding sequence and M and N region-encoding sequence or other coronavirus encoding sequence is cloned into a recombinant DNA vector, where it is expressed under the control of an inducible promoter, e.g., a heat shock promoter. [See, e.g., Wurm et al., *Proc. Natl. Acad. Sci. U.S.A.* 83:5414 (1986)]. Following induction of coronavirus, spike peptide, pol peptide or M and N region peptide expression, cell death is measured in experimental treatments involving the presence of an inhibitor candidate, and in appropriate positive and negative controls.

Antibodies

The spike peptide, pol peptide, M and N region peptide and coronavirus-encoding DNA of this invention enables one of ordinary skill in the art to produce anti-spike peptide, anti-pol peptide, anti-M and N region peptide and anti-coronavirus antibodies. The spike peptide, pol peptide, M and N region peptide and coronavirus-encoding DNA is used to construct a vector encoding a fusion protein comprising a spike peptide, pol peptide, M and N region peptide or coronavirus moiety and, preferably, an isolation-facilitating moiety, i.e., a moiety that can be readily isolated from contaminating proteins in an extract from a host cell used to express the fusion protein. A preferred isolation-facilitating moiety is maltose binding protein. DNA encoding maltose binding protein is commercially available. A binding reagent specific for the isolation-facilitating moiety is used for convenient and efficient isolation of the spike peptide and coronavirus fusion protein. For example, amylose chromatography is preferred for isolation of a fusion protein comprising maltose binding protein moiety. Following isolation, the spike peptide, pol peptide, M and N region peptide and coronavirus fusion protein is used to produce spike peptide, pol peptide, M and N region peptide and coronavirus-specific antibodies (polyclonal or monoclonal), according to standard methods, known to a person skilled in the art.

The anti-ferret coronavirus antibodies, anti-M and N region peptide antibodies, anti-pol peptide antibodies and anti-spike peptide antibodies of the invention have several uses. For example, they may be used as reagents for preparation of affinity chromatography media. Once the anti-coronavirus antibodies, anti-M and N region peptide antibodies, anti-pol peptide antibodies and anti-spike peptide antibodies of this invention are in hand, preparation of coronavirus affinity chromatography media can be carried out according to conventional methods known to a person skilled in the art, using commercially available reagents. The coronavirus-specific affinity chromatography media can be used to isolate coronavirus from natural sources or from host cells transformed with recombinant DNA encoding coronavirus. The anti-coronavirus antibodies, anti-M and N region peptide antibodies, anti-pol peptide antibodies and anti-spike peptide antibodies of the invention are also useful as analytical-scale laboratory reagents for research on the physiology and cell biology of coronavirus induced disease. For example, immunohistochemical techniques, based on anti-coronavirus antibodies, anti-M and N region peptide antibodies, anti-pol peptide antibodies and anti-spike peptide antibodies monoclonal antibodies are likely to be valuable tools for ECE diagnosis and treatment.

The anti-coronavirus antibodies, anti-M and N region peptide antibodies, anti-pol peptide antibodies and anti-spike peptide antibodies of the invention are also useful as diagnostic immunoassay reagents for measuring coronavirus levels in tissue samples from ferrets suspected of having ECE. Information on coronavirus levels in ferrets is a useful diagnostic or prognostic indicator in any situation where following the progression of ECE in individual animals or populations is merited.

Anti-coronavirus antibodies, anti-M and N region peptide antibodies, anti-pol peptide antibodies and anti-spike peptide antibodies may also be used for coronavirus detection in tissues. If the tissue sample is highly homogenous with respect to cell type, it may be preferable to carry out the ferret coronavirus, M and N region peptide, pol peptide and spike peptide immunoassay on an extract from a homogenate. Alternatively, it may be preferable to use an immunohistochemical assay involving anti-coronavirus antibodies, anti-M and N region peptide antibodies, anti-pol peptide antibodies and anti-spike peptide antibodies. An immunohistochemical assay is preferable when the tissue sample is heterogenous with respect to cell type. An immunohistochemical assay will yield information on the distribution of differing coronavirus levels in a cross section of tissue, or differing coronavirus levels in other various types of cells. Such information will allow for the monitoring of disease progression.

The anti-coronavirus antibodies, anti-M and N region peptide antibodies, anti-pol peptide antibodies and anti-spike peptide antibodies of the present invention can be used in various diagnostic immunoassay formats known in the art. Exemplary immunoassay formats are competitive radioimmunoassay, ELISA, Western blot analysis and microcapillary devices comprising immobilized antibody. [See, e.g., Dafforn et al., *Clin. Chem.* 36:1312 (1990); Li et al., *Anal. Biochem.* 166:276 (1987); Zuk et al., U.S. Pat. No. 4,435,504; Zuk et al., *Clin. Chem.* 31:1144 (1985); Tom et al., U.S. Pat. No. 4,366,241; and Clark, PCT published application WO 93/03176, all of which are herein incorporated by reference].

Expression Vectors

The ferret coronavirus, M and N region peptide, pol peptide and spike peptide-encoding DNA of this invention can be used as an in situ hybridization reagent to assess transcription of coronavirus and spike peptide genes and observe coronavirus, M and N region peptide, pol peptide and spike peptide RNA processing, for diagnostic purposes or research purposes.

A wide variety of host/expression vector combinations can be employed for expressing coronavirus, M and N region peptide, pol peptide and spike peptide-encoding DNA of this invention. The expression of coronavirus, M and N region peptide, pol peptide and spike peptide-encoding DNA in a cellular screening assay is preferably in a eukaryotic cell, under the control of eukaryotic expression control sequences. More preferably, the eukaryotic cell is a cultured mammalian cell. Even more preferable, the mammalian cell is a human cell. If the expression of recombinant coronavirus, M and N region peptide, pol peptide and spike peptide-encoding DNA is merely for the production of isolated recombinant coronavirus, M and N region peptide, pol peptide and spike peptide, however, a prokaryotic host/expression vector system or a eukaryotic host/expression system can be used.

I. Ferret Coronavirus, M and N Region Peptide, Pol Peptide and Spike Peptide Polynucleotides As described above, a novel coronavirus, the putative causative agent of ECE in ferrets, has been discovered and partly sequenced. Accordingly, the present invention provides nucleic acids encoding ferret coronavirus and specific peptides including, but not limited to, the spike peptide (SEQ ID NO: 4), the M and N region peptide (SEQ ID NO: 1), the pol peptide (SEQ ID NO: 12) and variants (e.g., polymorphisms and mutants), and fragments. In some embodiments, the present invention provides polynucleotide sequences that are capable of hybridizing to nucleotide sequences with homology to SEQ ID NOs: 1, 4 and 12 under conditions of low to high stringency as long as the polynucleotide sequence capable of hybridizing encodes a protein that retains at least one or a portion of at least one biological activity of a naturally occurring ferret coronavirus, M and N region peptide, pol peptide and spike peptide. In some embodiments, the protein that retains at least one or a portion of at least one biological activity of naturally occurring ferret coronavirus and spike peptide is 70% homologous to wild-type ferret coronavirus, M and N region peptide, pol peptide and spike peptide, preferably 80% homologous to wild-type ferret coronavirus, M and N region peptide, pol peptide and spike peptide, more preferably 90% homologous to wild-type ferret coronavirus, M and N region peptide, pol peptide and spike peptide, and most preferably 95% homologous to wild-type ferret coronavirus, M and N region peptide, pol peptide and spike peptide. In preferred embodiments, hybridization conditions are based on the melting temperature ($T_m$) of the nucleic acid binding complex and confer a defined "stringency" as explained above (See e.g., Wahl, et al., (1987) Meth. Enzymol., 152:399-407, incorporated herein by reference).

In other embodiments of the present invention, additional nucleotide sequences encoding coronavirus, M and N region peptide, pol peptide and spike peptide are contemplated. In preferred embodiments, nucleotide sequences result from a polymorphism or mutation (e.g., a change in the nucleic acid sequence) and generally produce altered mRNAs or polypeptides whose structure or function may or may not be altered. Any given nucleotide sequence may have none, one or many variant forms. Common mutational changes that give rise to sequence variants are generally ascribed to deletions, additions or substitutions of nucleic acids. Each of these types of changes may occur alone, or in combination with the others, and at the rate of one or more times in a given sequence. Non-limiting examples of the nucleotide sequences of the present invention include those encoded by SEQ ID NOS: 1, 4 and 12.

In other embodiments of the present invention, the nucleotide sequences of the present invention may be engineered in order to alter an ferret coronavirus, M and N region peptide, pol peptide and spike peptide coding sequence for a variety of reasons, including but not limited to, alterations which modify the cloning, processing and/or expression of the nucleotide sequence product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of ferret coronavirus, M and N region peptide, pol peptide and spike peptide may be extended utilizing the nucleotide sequences (e.g., SEQ ID NOS: 1, 4 and 12) in various methods known in the art to detect upstream sequences such as promoters and regulatory elements. For example, it is contemplated that restriction-site polymerase chain reaction (PCR) will find use in the present invention. This is a direct method which uses universal primers to retrieve unknown sequence adjacent to a known locus (Gobinda et al. (1993) PCR Methods Applic., 2:318-22). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al. (1988) Nucleic Acids Res., 16:8186). The primers may be designed using Oligo 4.0

(National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., (1991) Nucleic Acids Res., 19:3055-3060). The PROMOTERFINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in the case where an oligo d(T) library does not yield full-length cDNA. Genomic mammalian libraries are useful for obtaining introns and extending 5' sequence.

In other embodiments of the present invention, variants of the disclosed ferret coronavirus, M and N region peptide, pol peptide and spike peptide sequences are provided. In preferred embodiments, variants result from polymorphisms or mutations (e.g., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., ferret coronavirus, M and N region peptide, pol peptide and spike peptide binding function) for such purposes as altering (e.g., increasing or decreasing) the substrate specificity or selectivity affinity of the ferret coronavirus, M and N region peptide, pol peptide and spike peptide for its receptor or another substrate. Such modified peptides are considered functional equivalents of peptides having an activity of ferret coronavirus, M and N region peptide, pol peptide and spike peptide as defined herein. A modified peptide can be produced in which the nucleotide sequence encoding the polypeptide has been altered, such as by substitution, deletion, or addition. In particularly preferred embodiments, these modifications do not significantly reduce binding activity of the modified ferret coronavirus, M and N region peptide, pol peptide and spike peptide. In other words, construct "X" can be evaluated in order to determine whether it is a member of the genus of modified or variant ferret coronaviruses, M and N region peptides, pol peptides and spike peptides of the present invention as defined functionally, rather than structurally.

Moreover, as described above, variant forms of ferret coronavirus, M and N region peptide, pol peptide and spike peptide and nucleotides encoding the same are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of ferret coronavirus, M and N region peptide, pol peptide and spike peptide disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry,* pg. 17-21, 2nd ed, W H Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner. FIG. 3 shows examples of amino acids that can be chosen for substitution.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a ferret coronavirus and spike peptide coding sequence including, but not limited to, alterations that modify the cloning, processing, localization, secretion, and/or expression of the gene product. Such mutations may be introduced using techniques that are well known in the art (e.g., site-directed mutagenesis to insert new restriction sites, alter glycosylation patterns, or change codon preference, etc.).

II. Ferret Coronavirus, M and N Region Peptide, Pol Peptide and Spike Peptide Polypeptides In other embodiments, the present invention provides ferret coronavirus and spike peptide polypeptides and fragments. Non-limiting examples of ferret coronavirus, M and N region peptide and spike peptide polypeptides (e.g., SEQ ID NOS: 2, 3 and 5) are shown in FIG. 2. The pol peptide is encoded by the open reading frame of SEQ ID NO: 12. Other embodiments of the present invention provide fusion proteins or functional equivalents of these ferret coronavirus, M and N region peptide, pol peptide and spike peptide proteins. In still other embodiments, the present invention provides ferret coronavirus, M and N region peptide, pol peptide and spike peptide polypeptide variants, homologs, and mutants. In some embodiments of the present invention, the polypeptide is a naturally purified product, in other embodiments it is a product of chemical synthetic procedures, and in still other embodiments it is produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or it may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NO: 1, 4 and 12 which encode substantially the same or a functionally equivalent amino acid sequences, may be used to clone and express ferret coronavirus and spike peptide. In general, such polynucleotide sequences hybridize to SEQ ID NO: 1, 4 and 12 under conditions of high to medium stringency as described above. As will be understood by those of skill in the art, it may be advantageous to produce ferret coronavirus-, M and N region peptide-, pol peptide- and spike peptide-encoding nucleotide sequences possessing non-naturally occurring codons. Therefore, in some preferred embodiments, codons preferred by a particular prokaryotic or eukaryotic host (Murray et al. "Codon usage in plant genes," *Nucleic Acids Res.* 17:477-498, 1989) are selected, for example, to increase the rate of ferret coronavirus and spike peptide expression or to produce recombinant RNA transcripts having desirable properties, such as a longer half-life, than transcripts produced from naturally occurring sequence.

A. Vectors for Production of Ferret Coronavirus, M and N Region Reptide, Pol Peptide and Spike Peptide The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOS: 1, 4 and 12). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NOS: 1, 4 and 12) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene), Bac to Bac (Invirogen). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

B. Host Cells for Production of Ferret Coronavirus, M and N Region Peptide, Pol Peptide and Spike Peptide In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis,* and various species within the genera *Pseudomonas, Streptomyces,* and *Staphylococcus,* as well as *Saccharomycees cerivisiae, Schizosaccharomycees pombe, Drosophila* S2, cells, Spodoptera Sf9 cells, CRFK cells, HRT 18-G cells, primary ferret kidney cells, transformed ferret kidney cells, Chinese hamster ovary (CHO) cells, COS-7 lines of monkey kidney fibroblasts, (Gluzman, Cell 23:175, 1981), C127, 3T3, 293, 293T, HeLa and BHK cell lines, T-1 (tobacco cell culture line), root cell and cultured roots in rhizosecretion (Gleba et al., Proc Natl Acad Sci USA 96: 5973-5977, 1999).

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al. (1986) Basic Methods in Molecular Biology). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al. (2001) Molecular Cloning: A Laboratory Manual, Third Edition, Cold Spring Harbor, N.Y.

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

C. Purification of Ferret Coronavirus, M and N Region Peptide, Pol Peptide and Spike Peptide The present invention also provides methods for recovering and purifying ferret coronavirus, M and N region peptide, pol peptide and spike peptide from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having the coding sequence (e.g., SEQ ID NOS: 1, 4 and 12) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson, et al., "The structure of an antigenic determinant in a protein," Cell, 37:767-778, 1984).

D. Fragments and Domains of Ferret Coronavirus, M and N Region Peptide, Pol Peptide and Spike Peptide In addition, the present invention provides fragments of ferret coronavirus, M and N region peptide, pol peptide and spike peptide (i.e., truncation mutants, e.g., portions of SEQ ID NOS: 1, 4 and 12). In other embodiments, the present invention provides domains of ferret coronavirus, M and N region peptide, pol peptide and spike peptide (e.g., the binding domain). In some embodiments of the present invention, when expression of a portion of the ferret coronavirus, M and N region peptide, pol peptide and spike peptide is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol., 169:751) and Salmonella typhimurium and its in vitro activity has been demonstrated on recombinant proteins (Miller et al. (1990) Proc. Natl. Acad. Sci. USA 84:2718). Therefore, removal of an N-terminal methionine, if desired, can be achieved either in vivo by expressing such recombinant polypeptides in a host which produces MAP (e.g., E. coli or CM89 or S. cerevisiae), or in vitro by use of purified MAP.

E. Fusion Proteins Containing Ferret Coronavirus, M and N Region Peptide, Pol Peptide and Spike Peptide The present invention also provides fusion proteins incorporating all or part of ferret coronavirus, M and N region peptide, pol peptide and spike peptide. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a ferret coronavirus, M and N region peptide, pol peptide and spike peptide protein. In some embodiments of the present invention, the VP6 capsid protein of rotavirus is used as an immunologic carrier protein for portions of the ferret coronavirus, M and N region peptide, pol peptide and spike peptide polypeptide, either in the monomeric form or in the form of a viral particle. In other embodiments of the present invention, the nucleic acid sequences corresponding to the portion of ferret coronavirus, M and N region peptide, pol peptide and spike peptide against which antibodies are to be raised can be incorporated into a fusion gene construct which includes coding sequences for a late vaccinia virus structural protein to produce a set of recombinant viruses expressing fusion proteins comprising a portion of ferret coronavirus, M and N region peptide, pol peptide and spike peptide as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of ferret coronavirus, M and N region peptide, pol peptide and spike peptide and the poliovirus capsid protein are created to enhance immunogenicity of the set of polypeptide antigens (See e.g., EP Publication No. 025949; and Evans et al. (1989) Nature 339:385; Huang et al. (1988) J. Virol., 62:3855; and Schlienger et al. (1992) J. Virol., 66:2).

In still other embodiments of the present invention, the multiple antigen peptide system for peptide-based immunization can be utilized. In this system, a desired portion of ferret coronavirus, M and N region peptide, pol peptide and spike peptide is obtained directly from organo-chemical synthesis of the peptide onto an oligomeric branching lysine core (see e.g., Posnett et al. (1988) J. Biol. Chem., 263:1719; and Nardelli et al. (1992) J. Immunol., 148:914). In other embodiments of the present invention, antigenic determinants of the ferret coronavirus, M and N region peptide, pol peptide and spike peptide proteins can also be expressed and presented by bacterial cells.

In addition to utilizing fusion proteins to enhance immunogenicity, it is widely appreciated that fusion proteins can also facilitate the expression of proteins, such as the ferret coronavirus, M and N region peptide, pol peptide and spike peptide protein of the present invention. Accordingly, in some embodiments of the present invention, ferret coronavirus, M and N region peptide, pol peptide and spike peptide can be generated as a glutathione-S-transferase (i.e., GST fusion protein). It is contemplated that such GST fusion proteins will enable easy purification of ferret coronavirus, M and N region peptide, pol peptide and spike peptide, such as by the use of glutathione-derivatized matrices (See e.g, Ausabel et al. (1992) (eds.), Current Protocols in Molecular Biology, John Wiley & Sons, NY). In another embodiment of the present invention, a fusion gene coding for a purification leader sequence, such as a poly-(His)/enterokinase cleavage site sequence at the N-terminus of the desired portion of ferret coronavirus and spike peptide, can allow purification of the expressed ferret coronavirus, M and N region peptide, pol peptide and spike peptide fusion protein by affinity chromatography using a $Ni^{2+}$ metal resin. In still another embodiment of the present invention, the purification leader sequence can then be subsequently removed by treatment with enterokinase (See e.g., Hochuli et al. (1987) J. Chromatogr., 411:177; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

F. Variants of Ferret Coronavirus, M and N Region Peptide, Pol Peptide and Spike Peptide Still other embodiments of the present invention provide mutant or variant forms of ferret coronavirus, M and N region peptide, pol peptide and spike peptide. It is possible to modify the structure of a peptide having an activity of ferret coronavirus, M and N region peptide, pol peptide and spike peptide for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject ferret coronavirus, M and N region peptide, pol peptide and spike peptide proteins as defined herein. A modified peptide can be produced in which the amino acid sequence has been altered, such as by amino acid substitution, deletion, or addition. In one embodiment, the amino acid is altered to provide for coupling by conventional coupling chemistry (see, e.g., Example 8).

Moreover, as described above, variant forms (e.g., mutants or polymorphic sequences) of the subject ferret coronavirus, M and N region peptide, pol peptide and spike peptide proteins and the nucleotides encoding them are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present ferret coronavirus, M and N region peptide, pol peptide and spike peptide proteins, as well as truncation mutants, and is especially useful for identifying potential variant sequences (i.e., mutants or polymorphic sequences) that are functional in detecting mutant variants in vivo or in vitro. The purpose of screening such combinatorial libraries is to generate, for example, novel ferret coronavirus and spike peptide variants that can act as therapeutics.

Therefore, in some embodiments of the present invention, ferret coronavirus, M and N region peptide, pol peptide and spike peptide variants are engineered by the present method to provide altered substrate specificity or selectivity. In other embodiments of the present invention, combinatorially-derived variants are generated which have a selective potency relative to a naturally occurring ferret coronavirus, M and N region peptide, pol peptide and spike peptide. Such proteins, when expressed from recombinant DNA constructs, can be used in gene therapy protocols.

Still other embodiments of the present invention provide ferret coronavirus, M and N region peptide, pol peptide and spike peptide variants that have intracellular half-lives dramatically different than the corresponding wild-type protein. For example, the altered protein can be rendered either more stable or less stable to proteolytic degradation or other cellular process that result in destruction of, or otherwise inactivate ferret coronavirus, M and N region peptide, pol peptide and spike peptide. Such variants, and the genes which encode them, can be utilized to alter the location of ferret coronavirus, M and N region peptide, pol peptide and spike peptide expression by modulating the half-life of the protein. For instance, a short half-life can give rise to more transient ferret coronavirus and spike peptide biological effects and, when part of an inducible expression system, can allow tighter control of ferret coronavirus and spike peptide levels within the cell. Also, a long half-life can give rise to prolonged biological effects and have use as a therapeutic. As above, such proteins, and particularly their recombinant nucleic acid constructs, can be used in gene therapy protocols.

In some embodiments of the combinatorial mutagenesis approach of the present invention, the amino acid sequences for a population of ferret coronavirus and spike peptide homologs, variants or other related proteins are aligned, preferably to promote the highest homology possible. Such a population of variants can include, for example, ferret coronavirus, M and N region peptide, pol peptide and spike peptide homologs from one or more species, or ferret coronavirus, M and N region peptide, pol peptide and spike peptide variants from the same species but which differ due to mutation or polymorphisms. Amino acids that appear at each position of the aligned sequences are selected to create a degenerate set of combinatorial sequences.

In a preferred embodiment of the present invention, the combinatorial ferret coronavirus, M and N region peptide, pol peptide and spike peptide library is produced by way of a degenerate library of genes encoding a library of polypeptides which each include at least a portion of potential ferret coronavirus, M and N region peptide, pol peptide and spike peptide protein sequences. For example, a mixture of synthetic oligonucleotides can be enzymatically ligated into gene sequences such that the degenerate set of potential ferret coronavirus, M and N region peptide, pol peptide and spike peptide sequences are expressible as individual polypeptides, or alternatively, as a set of larger fusion proteins (e.g., for phage display) containing the set of ferret coronavirus and spike peptide sequences therein.

There are many ways by which the library of potential ferret coronavirus, M and N region peptide, pol peptide and spike peptide homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential ferret coronavirus, M and N region peptide, pol peptide and spike peptide sequences. The synthesis of degenerate oligonucleotides is well known in the art (See e.g., Narang (1983) Tetrahedron Lett., 39:39; Itakura et al. (1981) Recombinant DNA, in Walton (ed.), *Proceedings of the 3rd Cleveland Symposium on Macromolecules,* Elsevier, Amsterdam, pp 273-289; Itakura et al. (1984) Annu. Rev. Biochem., 53:323; Itakura et al. (1984) Science 198:1056; Ike et al. (1983) Nucl. Acid Res., 11:477). Such techniques have been employed in the directed evolution of other proteins (See e.g., Scott et al. (1980) Science 249:386; Roberts et al. (1992) Proc. Natl. Acad. Sci. USA 89:2429; Devlin et al. (1990) Science 249: 404; Cwirla et al. (1990) Proc. Natl. Acad. Sci. USA 87: 6378; as well as U.S. Pat. Nos. 5,223,409, 5,198,346, and 5,096,815; each of which is incorporated herein by reference).

It is contemplated that the ferret coronavirus, M and N region peptide, pol peptide and spike peptide nucleotide sequences (e.g., SEQ ID NO: 1 and 4, and fragments and variants thereof) can be utilized as starting nucleic acids for directed evolution. These techniques can be utilized to develop ferret coronavirus, M and N region peptide, pol peptide and spike peptide variants having desirable properties such as increased or decreased ferret coronavirus, M and N region peptide, pol peptide and spike peptide binding activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold (1996) Nat. Biotech., 14, 458; Leung et al. (1989) Technique, 1:11; Eckert and Kunkel (1991) PCR Methods Appl., 1:17-24; Caldwell and Joyce (1992) PCR Methods Appl., 2:28; and Zhao and Arnold (1997) Nuc. Acids. Res., 25:1307). After mutagenesis, the resulting clones are selected for desirable activity (e.g., screened for ferret coronavirus, M and N region peptide, pol peptide and spike peptide binding activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith (1994) Nature, 370:324; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer (1994) Nature, 370:398; Stemmer (1994) Proc. Natl. Acad. Sci. USA, 91:10747; Crameri et al. (1996) Nat. Biotech., 14:315; Zhang et al. (1997) Proc. Natl. Acad. Sci. USA, 94:4504; and Crameri et al. (1997) Nat. Biotech., 15:436). Variants produced by directed evolution can be screened for ferret coronavirus and spike peptide binding activity by the methods described in Example 1B.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of ferret coronavirus, M and N region peptide, pol peptide and spike peptide homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

G. Chemical Synthesis of Ferret Coronavirus, M and N Region Peptide, Pol Peptide and Spike Peptide In an alternate embodiment of the invention, the coding sequence of ferret coronavirus, M and N region peptide, pol peptide and spike peptide is synthesized, whole or in part, using chemical methods well known in the art (See e.g., Caruthers et al. (1980) Nucl. Acids Res. Symp. Ser., 7:215; Crea and Horn (1980) Nucl. Acids Res., 9:2331; Matteucci and Caruthers (1980) Tetrahedron Lett., 21:719; and Chow and Kempe (1981) Nucl. Acids. Res., 9:2807). In other embodiments of the present invention, the protein itself is produced using chemical methods to synthesize either an entire ferret coronavirus, M and N region peptide, pol peptide and spike peptide amino acid sequence or a portion thereof. For example, peptides can be synthesized by solid phase techniques, cleaved from the resin, and purified by preparative high performance liquid chromatography (See e.g., Creighton (1983) *Proteins Structures And Molecular Principles*, W H Freeman and Co, New York N.Y.). In other embodiments of the present invention, the composition of the synthetic peptides is confirmed by amino acid analysis or sequencing (See e.g., Creighton, supra).

Direct peptide synthesis can be performed using various solid-phase techniques (Roberge et al. (1995) Science 269: 202) and automated synthesis may be achieved, for example, using ABI 431A Peptide Synthesizer (Perkin Elmer) in accordance with the instructions provided by the manufacturer. Additionally, the amino acid sequence of ferret coronavirus, M and N region peptide, pol peptide and spike peptide, or any part thereof, may be altered during direct synthesis and/or combined using chemical methods with other sequences to produce a variant polypeptide.

III. Detection of Ferret Coronavirus, M and N Region Peptide, Pol Peptide and Spike Peptide Alleles A. Ferret Coronavirus, M and N Region Peptide, Pol Peptide and Spike Peptide Alleles In some embodiments, the present invention includes alleles of ferret coronavirus, M and N region peptide, pol peptide and spike peptide that correlate to infectability of ferret coronavirus leading to ECE in ferrets (e.g., including, but not limited to, the sequences shown in SEQ ID NOS: 2, 3 and 5 and the translation product of SEQ ID NO: 12).

The present invention is not limited to a particular mechanism of action. Indeed, an understanding of the mechanism of action is not necessary to practice the present invention. Nevertheless, it is contemplated that ferret coronavirus, M and N region peptide, pol peptide and spike peptide are involved in the binding of intestinal receptors in the ferret.

However, the present invention is not limited to the mutations described in the application. Any mutation that results in the undesired phenotype (e.g., an altered level of coronavirus binding, or the presence of or susceptibility to ECE) is within the scope of the present invention. For example, in some embodiments, the present invention provides alleles containing one or more single-nucleotide changes of ferret coronavirus, M and N region peptide, pol peptide and spike peptide sequences.

B. Detection of Variant Nucleotide Sequences

Accordingly, the present invention provides methods for determining whether an animal has a variant ferret coronavirus, M and N region peptide, pol peptide and spike peptide allele. In preferred embodiments, the variation is a mutation resulting in decreased or increased levels of ferret coronavirus, M and N region peptide, pol peptide and spike peptide or reduced or increased functionality of ferret coronavirus and spike peptide.

A number of methods are available for analysis of variant (e.g., mutant or polymorphic) nucleic acid sequences. Assays for detections polymorphisms or mutations fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

1. Direct Sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest is sequenced using any suitable method, including but not limited to manual sequencing using radioactive marker nucleotides, or automated sequencing. The results of the sequencing are displayed using any suitable method. The sequence is examined and the presence or absence of a given ferret coronavirus sequence is determined.

2. PCR Assays

In some embodiments of the present invention, variant sequences are detected using a PCR-based assay. In some embodiments, the PCR assay comprises the use of oligonucleotide primers that hybridize only to the variant or wild type allele of ferret coronavirus, M and N region peptide, pol peptide and spike peptide (e.g., to the region of polymorphism or mutation). Both sets of primers are used to amplify a sample of DNA. If only the mutant primers result in a PCR product, then the patient has the mutant ferret coronavirus, M and N region peptide, pol peptide and spike peptide allele. If only the wild-type primers result in a PCR product, then the patient has the wild type allele of ferret coronavirus, M and N region peptide, pol peptide and spike peptide.

3. Fragment Length Polymorphism Assays

In some embodiments of the present invention, variant sequences are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a SNP or a mutation will have a different banding pattern than wild type.

a. RFLP Assays

In some embodiments of the present invention, variant sequences are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assays

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

4. Hybridization Assays

In preferred embodiments of the present invention, ferret coronavirus sequences are detected a hybridization assay. In a hybridization assay, the presence of absence of a given sequence is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the ferret coronavirus sequence of interest is detected directly by visualizing a bound probe (e.g., a Northern or Southern assay; See e.g., Ausabel et al. (eds.) (1991) Current Protocols in Molecular Biology, John Wiley & Sons, NY). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the ferret coronavirus sequence being detected is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given ferret coronavirus sequence. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given ferret coronavirus sequence are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding.

In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the amidite A is delivered only to the sites where amidite A is to be coupled during that synthesis step and so on. Common reagents and washes are delivered by flooding the entire surface and then removing them by spinning.

DNA probes unique for the ferret coronavirus sequence of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given ferret coronavirus sequence. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments of the present invention, hybridization is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific ferret coronavirus sequences in unamplified genomic DNA. The isolated DNA sample is contacted with the first probe specific either for a SNP/mutation or wild type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

5. Mass Spectroscopy Assays

In some embodiments, a MassARRAY system (Sequenom, San Diego, Calif.) is used to detect variant sequences (See e.g., U.S. Pat. Nos. 6,043,031; 5,777,324; and 5,605,798; each of which is herein incorporated by reference). DNA is isolated from blood samples using standard procedures. Next, specific DNA regions containing the ferret coronavirus sequence of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged, when an electrical field pulse is subsequently applied to the tube the diagnostic product is launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 second including repetitive data collection. The SpectroTYPER software then calculates, records, compares and reports the genotypes at the rate of three seconds per sample.

6. Variant Analysis by Differential Antibody Binding

In other embodiments of the present invention, antibodies (See below for antibody production) are used to determine if an individual contains an allele encoding a ferret coronavirus, M and N region peptide, pol peptide and spike peptide nucleotide sequence containing a mutation. In preferred embodiments, antibodies are utilized that discriminate between mutant (i.e., truncated proteins); and wild-type proteins (e.g., SEQ ID NOS: 2, 3 and 5 and the translation product of SEQ ID NO: 12).

7. Kits for Analyzing Diagnosing ECE

The present invention also provides kits for determining the presence of ferret coronavirus, M and N region peptide, pol peptide or the spike peptide. The diagnostic kits are produced in a variety of ways. In some embodiments, the kits contain at least one reagent for specifically detecting a ferret coronavirus, M and N region peptide, pol peptide and spike peptide allele or protein. In some preferred embodiments, the kits contain reagents for detecting a SNP caused by a single nucleotide substitution of the wild-type gene. In these preferred embodiments, the reagent is a nucleic acid that hybridizes to nucleic acids containing the SNP and that does not bind to nucleic acids that do not contain the SNP. In other preferred embodiments, the reagents are primers for amplifying the region of DNA containing the SNP. In still other embodiments, the reagents are antibodies that preferentially bind either the ferret coronavirus and spike peptides. In some embodiments, the kits include ancillary reagents such as buffering agents, nucleic acid stabilizing reagents, protein stabilizing reagents, and signal producing systems (e.g., fluorescence generating systems as Fret systems). The test kit may be packages in any suitable manner, typically with the elements in a single container or various containers as necessary along with a sheet of instructions for carrying out the test. In some embodiments, the kits also preferably include a positive control sample.

IV. Generation of Ferret Coronavirus, M and N Region Peptide, Pol Peptide and Spike Peptide Antibodies Antibodies can be generated to allow for the detection of ferret coronavirus, M and N region peptide, pol peptide and spike peptide protein. The antibodies may be prepared using various immunogens. In one embodiment, the immunogen is a ferret coronavirus, M and N region peptide, pol peptide and spike peptide to generate antibodies that recognize ferret coronavirus, M and N region peptide, pol peptide and spike peptide. Such antibodies include, but are not limited to polyclonal, monoclonal, chimeric, single chain, Fab fragments, and Fab expression libraries.

Various procedures known in the art may be used for the production of polyclonal antibodies directed against ferret coronavirus, M and N region peptide, pol peptide and spike peptide. For the production of antibody, various host animals can be immunized by injection with the peptide corresponding to the ferret coronavirus, M and N region peptide, pol peptide and spike peptide epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). One approach to such conjugation is provided in Example 8. Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward ferret coronavirus, M and N region peptide, pol peptide and spike peptide, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein (1975) Nature 256:495-497), as well as the trioma technique, the human B-cell hybridoma (ferret B cells may be substituted) technique (See e.g., Kozbor et al. (1983) Immunol. Tod., 4:72), and the EBV-hybridoma technique to produce ferret monoclonal antibodies (Cole et al. (1985) in *Monoclonal Antibodies and Cancer Therapy*, Alan R. Liss, Inc., pp. 77-96).

In an additional embodiment of the invention, monoclonal antibodies are produced in germ-free animals utilizing technology such as that described in PCT/US90/02545). Furthermore, it is contemplated that ferret antibodies will be generated by ferret hybridomas (Cote et al. (1983) Proc. Natl. Acad. Sci. USA 80:2026-2030) or by transforming ferret B cells with EBV virus in vitro (Cole et al. (1985) in *Monoclonal Antibodies and Cancer Therapy*, Alan R. Liss, pp. 77-96).

In addition, it is contemplated that techniques described for the production of single chain antibodies (U.S. Pat. No. 4,946,778; herein incorporated by reference) will find use in producing ferret coronavirus and spike peptide specific single chain antibodies. An additional embodiment of the invention utilizes the techniques described for the construction of Fab expression libraries (Huse et al. (1989) Science 246:1275-1281) to allow rapid and easy identification of monoclonal Fab fragments with the desired specificity for ferret coronavirus, M and N region peptide, pol peptide and spike peptide.

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of ferret coronavirus and spike peptide (e.g., for Western blotting), measuring levels thereof in appropriate biological samples, etc. The antibodies can be used to detect ferret coronavirus, M and N region peptide, pol peptide and spike peptide in a biological sample from a ferret. The biological sample can be a biological fluid, such as, but not limited to, blood, serum, plasma, interstitial fluid, urine, cerebrospinal fluid, and the like, containing cells.

The biological samples can then be tested directly for the presence of ferret coronavirus, M and N region peptide, pol peptide and spike peptide using an appropriate strategy (e.g., ELISA or radioimmunoassay) and format (e.g., microwells, dipstick (e.g. as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of ferret coronavirus, M and N region peptide, pol peptide and spike peptide detected by immunoblotting (Western blotting). Immunoblotting techniques are generally more effective with antibodies generated against a peptide corresponding to an epitope of a protein, and hence, are particularly suited to the present invention.

In other embodiments, the antigen is a peptide fragment of ferret coronavirus, M and N region peptide, pol peptide and spike peptide; preferably, the fragment is of high antigenicity. In yet other embodiment, the immunogen is a variant or mutant of ferret coronavirus, M and N region peptide, pol peptide and spike peptide to generate antibodies that recognize the variant or mutant ferret coronavirus, M and N region peptide, pol peptide and spike peptide. Such antibodies include, but are not limited to polyclonal, monoclonal, chimeric, single chain, Fab fragments, and Fab expression libraries, and are prepared and used as described above. These antibodies can then be used to detect the presence of a fragment or variant or mutant ferret coronavirus, M and N region peptide, pol peptide and spike peptide in a biological sample from a ferret, as described above, and thus to diagnosis ECE.

For example, peptide antibodies may be synthesized against peptide in any one of the exons. Additionally, peptide fragments may be selected on the basis of determinations by computer algorithms and other methods as having high "antigenicity" (likely to elicit an immune response); the selected peptides were then synthesized. The peptide fragments are injected into rabbits, and the rabbits periodically bled and boosted with the peptide antigen between bleeds. This serum is used as the source of the antibodies, while the serum before peptide injection is used as a negative control. The antibodies are affinity purified by passing the serum over a column composed of the peptide to purify only antibodies that bind the peptide. At least one of these antibodies in the unpurified state detects a protein of approximately the right size that is present in normal plasma but not patient plasma. Antibodies are also prepared against other peptide fragments.

V. Methods of Treatment of ECE

A. Treatment with Antibodies

The present invention contemplates a method of treating ferrets with ECE by administering antibodies of the present invention to the afflicted ferret (or a ferret at risk for the disease, e.g., prophylactic treatment). Although the present invention is not limited to any particular theory, it is believed that the antibodies will bind the spike and M and N region peptides of the ferret coronavirus and thereby prevent the virus from binding to intestinal sites of the ferret.

B. Treatment with Modified Spike Peptides, Pol Peptides and M and N Region Peptides The present invention contemplates a method of treating ferrets with ECE by administering modified spike pol and M and N region peptides to the afflicted ferret. Although the present invention is not limited to any particular theory, it is believed that the modified peptides will bind to the intestinal binding sites of the ferret and prevent the ECE causing coronavirus from binding. The modified spike, pol and M and N region peptides would be altered so as to not induce ECE disease symptoms in the ferret.

VI. Drug Screening Using Ferret Coronavirus, M and N Region Peptide, Pol Peptide and Spike Peptide The present invention provides methods and compositions for using ferret coronavirus, M and N region peptide, pol peptide and spike peptide as a target for screening drugs that can alter, for example, ferret coronavirus, M and N region peptide, pol peptide and spike peptide binding activity and associated symptoms (e.g., ECE). For example, drugs that induce or inhibit ferret coronavirus, M and N region peptide, pol peptide and spike peptide binding activity can be identified by screening for compounds that target ferret coronavirus, M and N region peptide, pol peptide and spike peptide translation or regulate ferret coronavirus nucleotide transcription or replication. The present invention is not limited to a particular mechanism of action. Indeed, an understanding of the mechanism of action is not necessary to practice the present invention.

In one screening method, candidate compounds are evaluated for their ability to alter ferret coronavirus, M and N region peptide, pol peptide and spike peptide binding activity by adding the compound in the presence of ferret coronavirus, M and N region peptide, pol peptide and spike peptide to an assay for the ferret coronavirus, M and N region peptide, pol peptide and spike peptide binding activity and determining the effects of the compound on the level of ferret coronavirus, M and N region peptide, pol peptide and spike peptide binding activity.

Another technique uses ferret coronavirus, M and N region peptide, pol peptide and spike peptide antibodies, generated as discussed above. Such antibodies capable of specifically binding to ferret coronavirus, M and N region peptide, pol peptide and spike peptides can be used to detect the presence of any peptide that shares one or more antigenic determinants of the ferret coronavirus and spike peptide. Such peptides can then be evaluated for binding activity as described above.

The present invention contemplates a variety of other means of screening compounds. The examples provided above are presented merely to illustrate a range of techniques available. One of ordinary skill in the art will appreciate that many other screening methods can be used.

In particular, the present invention contemplates the use of cell lines transfected with ferret coronavirus, M and N region peptide, pol peptide and spike peptide and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in reporter gene assays that monitor cellular responses at the transcription/translation level. In still further embodiments, the cells can be used in cell proliferation assays to monitor the overall growth/no growth response of cells to external stimuli.

The cells are useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminescent products of specific substrates (e.g., X-gal and luciferin). Comparisons between compounds of known and unknown activities may be conducted as described above.

VII. Pharmaceutical Compositions Containing Ferret Coronavirus, M and N Region Peptide, Pol Peptide and Spike Peptide Nucleotides, Antibodies, Analogs and Drugs The present invention further provides pharmaceutical compositions which may comprise all or portions of ferret coronavirus (e.g., modified coronavirus), M and N region peptide, pol peptide and spike peptide polynucleotide sequences, ferret coronavirus, M and N region peptide, pol peptide and spike peptide polypeptides, inhibitors or antagonists of ferret coronavirus, M and N region peptide, pol peptide and spike peptide bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by a decreased ferret coronavirus, M and N region peptide, pol peptide and spike peptide binding activity. Drugs which act to decrease ferret coronavirus and spike peptide binding activity as discovered through screening methods described above, are administered.

Drugs can be administered to the patient intravenously in a pharmaceutically acceptable carrier such as physiological saline. Standard methods for intracellular delivery of drugs can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, ferret coronavirus, M and N region peptide, pol peptide and spike peptide nucleotides and ferret coronavirus, M and N region peptide, pol peptide and spike peptide antibodies can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, ferret coronavirus, M and N region peptide, pol peptide and spike peptide polynucleotide sequences or ferret coronavirus, M and N region peptide, pol peptide and spike peptide antibodies may be administered alone to ferrets subject to or suffering from ECE (i.e., as a treatment or a preventative).

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of ferret coronavirus and spike peptide inhibiting drug, e.g., may be that amount that results in lower ferret coronavirus and spike peptide binding activity comparable to untreated, ECE infected ferrets. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of ferret coronavirus, M and N region peptide, pol peptide and spike peptide, conditions indicated on the label may include treatment of condition related to ECE.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-5% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (including murine models) to achieve a desirable circulating concentration range that adjusts ferret coronavirus levels.

A therapeutically effective dose refers to that amount of drug that ameliorates or alleviates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual veterinarian in view of the patient to be treated. Dosage and administration are adjusted to provide sufficient levels of the active moiety or to maintain the desired effect. Additional factors which may be taken into account include the severity of the disease state; age, weight, and gender of the patient; diet; time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for ferret coronavirus, M and N region peptide, pol peptide and spike peptide than for the inducers or enhancers of ferret coronavirus, M and N region peptide, pol peptide and spike peptide. Administration to the bone marrow may necessitate delivery in a manner different from intravenous injections.

VIII. Transgenic Animals Expressing Ferret Coronavirus, M and N Region Peptide,Ppol Peptide and Spike Peptide Nucleotide Sequences and Homologs, Mutants, and Variants Thereof The present invention contemplates the generation of transgenic animals comprising an exogenous ferret coronavirus, M and N region peptide, pol peptide and spike peptide nucleotide sequences or homologs, mutants, or variants thereof. In preferred embodiments, the transgenic animal displays an altered phenotype as compared to wild-type animals. In some embodiments, the altered phenotype is the expression of mRNA for ferret coronavirus, M and N region peptide, pol peptide and spike peptide. In other embodiments, the altered phenotype is expression of a mutant ferret coronavirus, M and N region peptide, pol peptide and spike peptide. Methods for analyzing the presence or absence of such altered phenotypes include Northern blotting, mRNA protection assays, RT-PCR and detection of protein expression with antibodies.

The transgenic animals of the present invention find use in drug and treatment regime screens. In some embodiments, test compounds (e.g., a drug that is suspected of being useful to treat ECE) and control compounds (e.g., a placebo) are administered to the transgenic animals and the control animals or to cultures of primary cells from the transgenic animals and the effects evaluated. The effects of the test and control compounds on disease symptoms are then assessed.

The transgenic animals can be generated via a variety of methods. In some embodiments, embryonic cells at various developmental stages are used to introduce transgenes for the production of transgenic animals. Different methods are used depending on the stage of development of the embryonic cell. The zygote is the best target for micro-injection. In the mouse, the male pronucleus reaches the size of approximately 20 micrometers in diameter which allows reproducible injection of 1-2 picoliters (pl) of DNA solution. The use of zygotes as a target for gene transfer has a major advantage in that in most cases the injected DNA will be incorporated into the host genome before the first cleavage (Brinster et al. (1985) Proc. Natl. Acad. Sci. USA 82:4438-4442). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich (1976) Proc. Natl. Acad. Sci. USA 73:1260). Efficient infection of the blastomeres is obtained by enzymatic treatment to remove the zona pellucida (Hogan et al. (1986) in *Manipulating the Mouse Embryo,* Cold Spring Harbor Laboratory Press, Cold Spring Harbor, N.Y.). The viral vector system used to introduce the transgene is typically a replication-defective retrovirus carrying the transgene (Jahner et al. (1985) Proc. Natl. Acad Sci. USA 82:6927). Transfection is easily and efficiently obtained by culturing the blastomeres on a monolayer of virus-producing cells (Van der Putten, supra; Stewart, et al. (1987) EMBO J., 6:383). Alternatively, infection can be performed at a later stage. Virus or virus-producing cells can be injected into the blastocoele (Jahner et al. (1982) Nature 298:623). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al. (1982) supra). Additional means of using retroviruses or retroviral vectors to create transgenic animals known to the art involves the microinjection of retroviral particles or mitomycin C-treated cells producing retrovirus into the perivitelline space of fertilized eggs or early embryos (PCT International Application WO 90/08832 [1990], and Haskell and Bowen (1995) Mol. Reprod. Dev., 40:386).

In other embodiments, the transgene is introduced into embryonic stem cells (ES) and the transfected stem cells are utilized to form an embryo. ES cells are obtained by culturing pre-implantation embryos in vitro under appropriate conditions (Evans et al. (1981) Nature 292:154; Bradley et al. (1984) Nature 309:255; Gossler et al. (1986) Proc. Acad. Sci. USA 83:9065; and Robertson et al. (1986) Nature 322:445). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoele of a blastocyst-stage embryo and contribute to the germ line of the resulting chimeric animal (for review, See, Jaenisch (1988) Science 240:1468). Prior to the introduction of transfected ES cells into the blastocoele, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoele.

In still other embodiments, homologous recombination is utilized knock-out gene function or create deletion mutants. Methods for homologous recombination are described in U.S. Pat. No. 5,614,396, incorporated herein by reference.

IX. Screens to Identify Ferret Coronavirus, M and N Region Peptide, Pol Peptide and Spike Peptide Interactive Molecules There are several different approaches contemplated by the present invention to look for small molecules that specifically bind ferret coronavirus, M and N region peptide, pol peptide and spike peptide and interact with ferret coronavirus, M and N region peptide, pol peptide and spike peptide. One approach is to transfect expression constructs comprising nucleic acid encoding ferret coronavirus, M and N region peptide, pol peptide and spike peptide into cells. Ferret coronavirus, M and N region peptide, pol peptide and spike peptide, along with any interactive molecules could then be precipitated and identified. Cells may be transiently transfected or stably transfected with the construct under control of an inducible promoter. Other embodiments would include translation of the invention and purification of the peptide. The purified peptide could then be used to test specific compound: protein interactions. Additionally, it is possible to generate antibodies to the translated invention allowing for the development of immunological assays such as, but not limited to, RIA, ELISA or Western blot. Furthermore, transgenic animals could be produced allowing for in vivo assays to be conducted.

A. In vitro Assays a. Transfection Assays

Transfection assays allow for a great deal of flexibility in assay development. The wide range of commercially available transfection vectors will permit the expression of the ferret coronavirus, M and N region peptide, pol peptide and spike peptide sequences of the present invention in a extensive number of cell types. In one embodiment, cells are transiently transfected with an expression construct comprising nucleic acid encoding ferret coronavirus, M and N region peptide, pol peptide and spike peptide that includes an inducible promotor allowing for the initiation of translation and transcription when needed. Cells would be exposed to the agent suspected of modulating ferret coronavirus, M and N region peptide, pol peptide and spike peptide expression and expression would be turned on and would be measured. Rates of ferret coronavirus, M and N region peptide, pol peptide and spike peptide expression in cells expressing the invention are compared to rates of expression in cells transfected with a control expression vector (e.g., an empty expression vector). Rates of expression can be quantitated by any of a number of ways reported in the literature and known to those practiced in the art.

In another embodiment, stably transfected cells lines are developed, i.e., cell lines stably expressing the ferret coronavirus, M and N region peptide, pol peptide and spike peptide mutants of the present invention. The use of an inducible promoter would be utilized in these systems. Screening assays for compounds suspected of modulating ferret coronavirus, M and N region peptide, pol peptide and spike peptide binding activity would be conducted in the same manner as with the transient transfection assays. Using stably transfected cell lines would allow for greater consistency between experiments and allow for inter-experimental comparisons.

b. Immunoprecipitation

After the generation of antibodies to ferret coronavirus, M and N region peptide, pol peptide and spike peptide, cells expressing transfected ferret coronavirus, M and N region peptide, pol peptide and spike peptide are lysed and then incubated with one of the antibodies. Antibodies with the bound ferret coronavirus, M and N region peptide, pol peptide and spike peptide and any associated proteins can then be pulled down with protein-A Sepharose or protein-G Sepharose beads, using standard techniques.

c. Fusion Protein Pull-Down

A method similar to immunoprecipitation is to construct fusion proteins of the ferret coronavirus and spike peptide and glutathione S-transferase (GST). The ferret coronavirus, M and N region peptide, pol peptide and spike peptide fusion proteins are then incubated with cell extracts and then removed with glutathione Sepharose beads. Any bound, ferret coronavirus and spike peptides are then characterized.

B. In Vivo Assays a. Yeast Two-Hybrid System

The yeast two-hybrid system that identifies the interaction between two proteins by reconstructing active transcription factor dimers. The dimers are formed between two fusion proteins, one of which contains a DNA-binding domain (DB) fused to the first protein of interest (DB-X) and the other, an activation domain (AD) fused to the second protein of interest (AD-Y). The DB-X:AD-Y interaction reconstitutes a functional transcription factor that activates chromosomally-integrated reporter genes driven by promoters containing the relevant DB binding sites. Large cDNA libraries can be easily screened with the yeast-two hybrid system. Yeast cDNA libraries are commercially available. Standard molecular biological techniques can be employed to isolate and characterize the interacting protein.

b. Transgenic Animal Assays

In one embodiment transgenic animals will be constructed using standard protocols (see, for example, Sambrooke, et al.). The generation of transgenic animals will allow for the investigation of diseases for which the mutated forms of ferret coronavirus, M and N region peptide, pol peptide and spike peptide may provide the means for determining the physiology of the disease or its treatment.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); L (liters); ml (milliliters); µl (microliters); cm (centimeters); mm (millimeters); µm (micrometers); nm (nanometers); ° C. (degrees Centigrade); RDA (representational difference analysis); nts (nucleotides); n (number); gDNA (genomic DNA).

Example 1

Study population. Medical records of ferrets with non-specific enteritis diagnosed between March 1993 and July 1999 on the basis of histologic examination of biopsy or necropsy specimens were reviewed at the Armed Forces institute of Pathology and AccuPath Inc. Criteria for inclusion in the study included a clinical history of diarrhea, lack of a definitive cause of the disease, and one or more of the following microscopic lesions: vacuolar degeneration and necrosis of villus enterocytes; villus atrophy, fusion, and blunting; and lymphoplasmacytic enteritis characterized by a subjective increase in number of intraepithelial lymphocytes. Of 171 reviewed cases, 110 met study criteria. In addition, 10 ferrets from a large breeding colony affected by an epizootic diarrheal disease were submitted to Purdue University for examination. After necropsy and microscopic examination, 9 of these ferrets met study criteria and were included in the study. Medical records were reviewed for history, clinical findings, and results of necropsy and laboratory tests. Because many of the medical records consisted primarily of pathology reports, complete clinicopathologic data were often not available. Biopsy and necropsy specimens were retrieved for histologic, immunohistochemical, electron microscopic, and immunofluorescent studies as well as virus isolation. Specimens from 5 control ferrets that did not meet study criteria were also obtained. Mean and median age of ferrets with ECE was 4.18 and 4.0 years, respectively. Because medical records were often incomplete, meaningful interpretation of other data was not possible.

Example 2

Breeding colony outbreak and disease characterization. Ten ferrets examined at Purdue University were submitted during a widespread outbreak of ECE in a large breeding colony. The disease spread from cage to adjacent cage but was also detected at more distant locations within 48 hours of appearance of the initial cases. Once clinical signs were noticed in ferrets in a given area, the disease progressed during a period of several weeks to affect ferrets in all cages within the same building. Initial attempts to contain the disease by use of protective clothing and restricted movement of ferret caretakers were unsuccessful. Palliative treatments such as administration of broad-spectrum antimicrobials and SC administration of fluids were used, depending on severity of clinical signs. Morbidity was initially limited to adult ferrets; mortality rate in most buildings was <5%. Within several weeks the epizootic subsided, although loose mucoid feces, without other clinical signs, were intermittently noticed in otherwise healthy young ferrets.

Gross lesions in ferrets with acute ECE were characterized by bright green diarrhea with high mucus content and hyperemia of affected portions of the small intestine. Ferrets examined at a later stage of disease had thinning of the intestinal wall with loss of villi, and the lumen contained grainy material described as resembling bird seed.

Microscopic lesions in affected ferrets were characterized by diffuse lymphocytic enteritis only (n=40), characterized by variable numbers of intraepithelial lymphocytes, or had lymphocytic enteritis as well as villus atrophy, fusion, and blunting, vacuolar degeneration and necrosis of the apical epithelium, or a combination of all these lesions (15). Lymphocytic enteritis, villus lesions, and diffuse mucosal necrosis with granulation tissue formation and bacteria were detected in 4 ferrets. Villus atrophy, fusion, and blunting was detected without other lesions in 3 ferrets and with vacuolar epithelial degeneration and necrosis only in 2 ferrets. Control ferrets had normal findings or lesions associated with other diseases.

Example 3

Immunohistochemical microscopy. Tissue preparation was performed as follows. Tissues were fixed in neutral buffered 10% formalin, embedded in paraffin, sectioned at 7 µm on a microtome, and stained with hematoxylin and eosin for examination by use of light microscopy.

Immunohistochemical studies were preformed as follows. Formalin-fixed paraffin-embedded tissues from 15 ferrets were selected for immunohistochemical evaluation. Two staining protocols and 2 types of antibodies were used. Following deparaffinization, 2 histologic slides of affected small intestine from each of 10 ferrets examined at the Armed Forces Institute of Pathology were washed in automation buffer with 10% acetone and 0.15% 23-lauryl ether and immersed in 3.0% hydrogen peroxide in methanol for 10 minutes to block endogenous peroxidase activity. After washing with automation buffer, slides were incubated in 0.05% protease XIV for 20 minutes at 42° C. Nonspecific antibody binding was blocked with 4% normal goat serum. Immunostaining was performed by overnight incubation at 4° C. with monoclonal antibody 7-3 (dilutions, 1:8,000 and 1:16,000) that had been produced against feline infectious peritonitis virus (this antibody also has cross-reactivity to canine and porcine coronavirus in formalin-fixed tissue) and biotinylated goat anti-mouse secondary antibody (dilution, 1:400). Staining was completed by use of a peroxidase labeled avidin-biotin complex followed by diaminobenzidine as a chromogen substrate. After a final washing in automation buffer, sections were counterstained with hematoxylin and eosin.

In the second protocol, following deparaffinization, 2 histologic slides of affected small intestine from each of 5 ferrets examined at Purdue University were washed in a mixture of 1 L of phosphate buffered saline solution and 50 μl Tween 201 (pH, 7.4) and immersed in 3.0% hydrogen peroxide for 10 minutes to block endogenous peroxidase activity. After washing with distilled water, slides were incubated in 10 mM EDTA/NaOH buffer (pH, 8.0) in a microwave oven (600 W) for 10 minutes and acclimatized at 20° C. for 60 minutes. Nonspecific antibody binding was blocked with 2% normal goat serum, monoclonal antibody FCV3-70 (this antibody reacts specifically with feline, canine, and porcine coronaviruses in paraffin-embedded tissue) was applied at a dilution of 1:100 followed by a 1:500 dilution of a biotinylated goat anti-mouse secondary antibody for overnight incubation at −4° C. Antibody binding was localized with a peroxidase-labeled avidin-biotin complex and stained with vector red alkaline phosphatase substrate. After washing in distilled water, sections were counterstained with Mayer's hematoxylin, dehydrated, cleared, and mounted in epoxy resin. Negative antibody control slides were prepared by staining tissue sections with isotype murine monoclonal control antibodies in both protocols.

Positive results of the immunohistochemical procedures were detected in 6 of 10 specimens from the Armed Forces Institute of Pathology by use of monoclonal antibody 7-3 and in 4 of 5 specimens from Purdue University by use of monoclonal antibody FCV3-70.

Specimens of small intestine from 9 ferrets from the large breeding colony were snap frozen with solid $CO_2$; 6 μm cryosections were cut, mounted on cover slips, air-dried, and fixed with acetone. After washing with Tris buffer (pH, 8.7), sections were incubated with fluorescein isothiocyanate-conjugated antibodies against canine distemper virus, canine parvovirus 2, canine coronavirus, canine herpesvirus, P bovine coronavirus, bovine rotavirus, porcine rotavirus, porcine hemagglutinating encephalomyelitis virus q and porcine transmissible gastroenteritis virus, P at a dilution of 1:500 for 30 minutes at 20° C. in a humid chamber. Unbound stain was removed by washing with Tris buffer. Sections were counterstained with Evans blue in Tris buffer (dilution, 1:10,000), mounted in glycerol, and examined by use of ultraviolet light microscopy.

Positive labeling for coronavirus ranged from staining of focal scattered villus enterocytes to staining of extensive numbers of enterocytes throughout the length of the villus. Results were negative for specimens from 5 control ferrets that were healthy or had intestinal diseases that were not caused by viruses.

Isolation of viruses from various tissues was attempted. Fecal extracts and tissue homogenates of spleen, liver, lung, and intestine from 9 acutely infected ferrets from the large breeding colony were passed through a 0.45 μm millipore filter and inoculated into the following cell cultures: MV-I-LU, HRT-18, DK-5966, CRSK, and A72-163. Identical inoculations were performed on cell cultures treated with trypsin and untreated cell cultures. These immunofluorescent and virus isolation studies by direct fluorescent antibody were done on frozen sections of intestine They were negative for canine distemper virus, canine parvovirus 2, canine coronavirus, canine herpesvirus, bovine coronavirus, bovine rotavirus, porcine rotavirus, porcine hemagglutinating encephalomyelitis virus, and porcine transmissible gastroenteritis virus. No viruses were isolated from intestine, spleen, lung or liver specimens.

Example 4

Electron microscopy. Fecal samples from 9 ferrets from the large breeding colony were diluted to approximately 5% with deionized water and centrifuged at 10,000 rpm for 5 minutes. The supernatant was removed and centrifuged at 20,000 rpm or 40 minutes; the resulting supernatant was discarded. A solution of 3 drops of 3% phosphotungstic acid, 1 drop of 0.1% bovine serum albumin, and enough deionized water to fill the appropriate number of spots on the spot plate was prepared, and 1 spot was pipetted into the tube to resuspend the pellet. The resuspended material was pipetted into a nebulizer and sprayed on grids; spraying was repeated 30 to 40 times on each grid. The nebulizer was removed, and grids were examined and photographed by use of a transmission electron microscope.

These studies showed Coronavirus-like particles, approximately 120 nm in diameter, were observed by use of transmission electron microscopy in fecal samples from 9 ferrets with ECE. Virions were characterized by an evenly spaced array of 20-nm pinshaped peplomers distributed around the periphery.

For the intestinal studies, specimens of small intestine from 2 affected ferrets from the large breeding colony were fixed sequentially in neutral-buffered 10% formalin and 4% glutaraldehyde and osmium tetroxide, embedded in epoxide resin, sectioned with an ultramicrotome, and stained with lead citrate and uranyl acetate. Sections were examined and photographed by use of a transmission electron microscope.

Transmission electron microscopy of selected sections of jejunal mucosa from 2 ferrets revealed highly pleomorphic virions, approximately 120 nm in diameter, in cytoplasmic vacuoles of apical enterocytes. Similar virions were found at the cell surface. The brush border of multiple apical enterocytes was degenerate or absent. Affected cells had degranulated endoplasmic reticulum, contained large numbers of intracytoplasmic vacuoles, or were shrunken.

Example 5

Extraction of RNA. Fecal samples were obtained from ferrets clinically diagnosed with epizootic catarrhal enteritis (ECE). RNA from fecal material was extracted by using the QIAGEN RNeasy Mini Kit (Valencia, Calif.) by adopting the RNeasy protocol for animal tissues (RNeasy Mini Handbook, 3rd edition, June 2001). 150 μl of diarrheic feces was processed with 450 ml of lysis buffer (Buffer RLT). Total sample RNA was eluted in 50 μl of RNase-free sterile water.

Example 6

RT-PCR Protocol. Degenerate universal coronavirus primers were used to amplify portions of the spike, M glycoprotein and N (nucleocapsid) genes (Tobler, K. and M. Ackermann, *Schweizer Archiv für Tierheilkunde,*138,80-86, 1996). Primer 55, 5' GGAKAAGGTKAATGARTGYGT 3' (SEQ ID NO: 6), and primer 56, 5' CCAKACVTACCAWG-GCCAYTT 3' (SEQ ID NO: 7), amplified a 628 nucleotide region of the ferret coronavirus spike gene. Primer 24, 5' CTCGAGCGACCCAGAMGACWCCKTC 3' (SEQ ID NO: 8), and primer 25, 5' GACTAGTTGGTGGAGWTT-TAAYCCWGA 3' (SEQ ID NO: 9), amplified a 735 nucleotide region spanning the 3' terminus of the M gene to the 5' terminus of the N gene. RT-PCR was performed using the QIAGEN OneStep RT-PCR Kit with 0.6 µM of each primer. Cycling conditions for both spike and N-M region amplifications were as follows: cDNA synthesis at 45° C. for 45 min, followed by pre-denaturation at 95° C. for 15 min; this was followed by 50 cycles of denaturation at 94° C. for 30 sec, annealing at 45° C. for 1 min, and extension at 72° C. for 2 min and 30 sec; a final extension of 72° C. for 7 min was added after the last PCR cycle. PCR products were analyzed by agarose gel electrophoresis and visualized by UV transillumination of ethidium bromide stained gels.

Additionally, a pair of degenerate primers was used to amplify a 251 bp region of the coronavirus polymerase gene at open reading frame (ORF) 1b: forward primer 5'-ACT-CARWTRAATYTNAAATAYGC-3' (SEQ ID NO: 10) and reverse primer 5'-TCACAYTTWGGATARTCCCA-3' (SEQ ID NO: 11) (Stephensen, C. B., et al., Virus Research, 60, 181-189, 1999). RT-PCR was performed using the QIAGEN OneStep RT-PCR Kit with 0.6 µM of each primer. Cycling conditions were as follows: cDNA synthesis at 40° C. for 45 min, followed by pre-denaturation at 95° C. for 15 min; this was followed by 5 cycles of denaturation at 94° C. for 1 min, 40° C. for 2 min, and 72° C. for 1 min; then 40 cycles of PCR at 94° C. for 1 min, 50° C. for 1.5 min and 72° C. for 1 min; with a final extension of 72° C. for 10 min. The product was analyzed by agarose gel electrophoresis, purified and cloned for sequencing (SEQ ID NO: 12; see, FIG. 4).

Furthermore, gene-specific primers were designed from the polymerase (pol) and spike sequence data obtained for the ferret coronavirus using the primer analysis software, OLIGO 6 (Molecular Biology Insights, Inc.). Forward primer, 5'-ATGGCTGTCTTATGGGTTGCC-3' (SEQ ID NO: 13), derived from pol sequence data, and reverse primer 5'-GCCAGACCACGCTGTTACACT-3' (SEQ ID NO: 14), derived from the spike sequence data (VA strain) (SEQ ID NO: 15; see, FIG. 5), were used to amplify a 10 kb region spanning a 3' section of the polymerase gene to the spike gene (region of already known sequence). Reverse transcription was performed with Omniscript Reverse Transcriptase (QIAGEN, Valencia, Calif.) according to the manufacture's recommendations. PCR amplification was carried out using Expand Long Template PCR system (Roche, Mannheim, Germany) as recommended. The product will be cloned using the QIAGEN PCR Cloning kit. Recombinant plasmid will be sent for automated sequencing to derive the remainder of the 5' sequence of the spike gene.

Example 7

An RT-PCR Assay Specific for the Detection of FECV. This reverse transcription-polymerase chain reaction (RT-PCR) assay is used to detect FECV RNA from feces, saliva and intestinal tissues. A variety of formats are possible. For example, the assay can be performed in either a gel-based format or in real-time using the fluorescent dye, SYBR Green I. RNA from clinical samples are extracted using the QIAGEN RNeasy Mini Kit (Valencia, Calif.). RNA is eluted out from the column with 50 µl of RNAse-free water. The primers used for this assay are as follows: forward primer 5'ACA GGT GGT TCT TTT ACT ACC 3' (SEQ ID NO: 18) and reverse primer 5' TGT AGG CAC AGT TTT AGC AC 3' (SEQ ID NO: 19). These primers target a 113 bp region of the FECV capsid gene.

The QIAGEN OneStep™ RT-PCR kit is used for the gel-based assay with an optimal primer concentration of 0.6 µM for each primer, for a final reaction volume of 50 µl. Five microliters of the extracted RNA template is used. The reaction mix does not require the addition of the Q™ solution from the kit. In one embodiment, the optimized cycling conditions are as follows: cDNA synthesis at 50° C. for 30 min, then a predenaturation at 95° C. for 15 min; this is followed by 40 PCR cycles of 94° C. for 30 sec, 53° C. for 30 sec(annealing step), and 72° C. for 1 min; with a final extension step of 72° C. for 7 min after the last PCR cycle.

The QuantiTect SYBR Green RT-PCR™ Kit (QIAGEN) is used to run the assay in real-time format. This kit is also a one-step kit which allows both reverse transcription and PCR to take place in a single tube. In one embodiment, optimal primer concentration is at 0.5 µM for each primer, for a final reaction volume of 50 µl. Five microliters of the extracted RNA template is used. Real-time RT-PCR is performed using the BIO-RAD iCycler/iCyler iQ™ Real-Time Detection System Software v 2.3B (BIO-RAD Laboratories, Hercules, Calif.), which incorporates a well-factor collection cycle prior to the run and a product melt cycle after the run. Cycling conditions are the same as above but annealing is extended for another 30 sec. and the final extension step at 72° C. for 7 min may be omitted.

Example 8

Cloning and Sequencing. The products were extracted from the gel using the QIAquick Gel Extraction Kit (QIAGEN). The purified products were TA-cloned into a plasmid vector using the QIAGEN PCR Cloning Kit. The inserts were amplified with M13 forward and reverse primers which prime the cloning vector at the appropriate positions just outside the multiple cloning site. PCR products were sent to the Genomic Technology Support Facility of Michigan State University for automated sequencing. Sequence data was analyzed using the Lasergene Biocomputing Software by DNASTAR, Inc. (Madison, Wis.). Nucleotide sequences (SEQ ID NOS: 1 nd 4) are shown in FIG. 1 and amino acid sequences (SEQ ID NOS: 2, 3 and 5) are show in FIG. 2.

Example 9

Conjugation of coronavirus-containing peptides. In this example, the preparation of a peptide conjugate is described. The coronavirus peptide can be prepared commercially (e.g. Multiple Peptide Systems, San Diego, Calif.) or isolated. The cysteine is added to facilitate conjugation to other proteins.

In order to prepare a protein for conjugation (e.g. BSA), it is dissolved in buffer (e.g., 0.01 M $NaPO_4$, pH 7.0) to a final concentration of approximately 20 mg/ml. At the same time n-maleimidobenzoyl-N-hydroxysuccinimide ester ("MBS" available from Pierce) is dissolved in N,N-dimethyl formamide to a concentration of 5 mg/ml. The MBS solution, 0.51 ml, is added to 3.25 ml of the protein solution and incubated for 30 minutes at room temperature with stirring every 5 minutes. The MBS-activated protein is then purified by chromatography on a Bio-Gel P-10 column (Bio-Rad; 40 ml bed volume) equilibrated with 50 mM NaPO$_4$, pH 7.0 buffer. Peak fractions are pooled (6.0 ml).

The above-described cysteine-modified peptide (20 mg) is added to the activated protein mixture, stirred until the peptide is dissolved and incubated 3 hours at room temperature. Within 20 minutes, the reaction mixture becomes cloudy and precipitates form. After 3 hours, the reaction mixture is centrifuged at 10,000×g for 10 min and the supernatant analyzed for protein content. The conjugate precipitate is washed three times with PBS and stored at 4° C.

Although the conjugation method described above is not limited to any particular use, it may be used to, for example, to add known immunogens to the peptides of the present invention, or portions thereof, to increase immugenicity of the peptide for the production of antibodies or for the use as a vaccine.

From the forgoing, it should be obvious that the disclosed invention provides novel nucleotide sequences, compounds and methods for the detection, diagnosis, treatment and preventative treatment of ferret ECE.

SEQUENCE LISTING

<160> NUMBER OF SEQ ID NOS: 19

<210> SEQ ID NO 1
<211> LENGTH: 735
<212> TYPE: DNA
<213> ORGANISM: Enteric coronavirus

<400> SEQUENCE: 1

```
gactagttgg tggagtttta accctgaaac caacgcaatc ttgtgtctta gtgcagtagg      60
aaaaagattt gtattaccac taaatggtgc gcctacaggt gttacgttga cacttttgtc    120
aggtaactta tatgctgaag gcttcaaggt tggaagtggt gtaaatgtcg ataacctacc    180
caagtacatt atggtagcca cacctggtaa tactattata tatcaccaag ttggcaagtc    240
tcttaaagca tccagtgcga ctggttggtc atactatgtc cgagctaaag caggcgatta    300
ctcaacagaa gcaagacaag atcatttgag tgaacacgaa aaactgttac atatggtata    360
agaactaaac ttctatcatg gctggaaacg acaacgtgt taactggggg gacgaacctg    420
ctccttcaca gaagcgtggt cgttctcgtt cccgttcccg ccgtaatgct gatataccat    480
tgtcatattt caaccctatt acccatgaag gtaagaagcc cttttggact gtagcaccaa    540
aagatttcgt gcctattggt aagggaaata aggaccaaca agtaggttat tggaatagac    600
agcaacgtta ccgcattcaa aagggtcaaa agtggactt accagacagg tggttctttt    660
actacctagg aactggtcca catagcaatg ctaaatttaa ggaccgtatt gaaggagtct    720
tctgggtcgc tcgag                                                      735
```

<210> SEQ ID NO 2
<211> LENGTH: 119
<212> TYPE: PRT
<213> ORGANISM: Enteric coronavirus

<400> SEQUENCE: 2

```
Thr Ser Trp Trp Ser Phe Asn Pro Glu Thr Asn Ala Ile Leu Cys Leu
1               5                   10                  15

Ser Ala Val Gly Lys Arg Phe Val Leu Pro Leu Asn Gly Ala Pro Thr
            20                  25                  30

Gly Val Thr Leu Thr Leu Leu Ser Gly Asn Leu Tyr Ala Glu Gly Phe
        35                  40                  45

Lys Val Gly Ser Gly Val Asn Val Asp Asn Leu Pro Lys Tyr Ile Met
    50                  55                  60

Val Ala Thr Pro Gly Asn Thr Ile Ile Tyr His Gln Val Gly Lys Ser
65                  70                  75                  80

Leu Lys Ala Ser Ser Ala Thr Gly Trp Ser Tyr Tyr Val Arg Ala Lys
                85                  90                  95

Ala Gly Asp Tyr Ser Thr Glu Ala Arg Gln Asp His Leu Ser Glu His
```

-continued

```
            100                 105                 110

Glu Lys Leu Leu His Met Val
        115

<210> SEQ ID NO 3
<211> LENGTH: 119
<212> TYPE: PRT
<213> ORGANISM: Enteric coronavirus

<400> SEQUENCE: 3

Met Ala Gly Asn Gly Gln Arg Val Asn Trp Gly Asp Glu Pro Ala Pro
1               5                   10                  15

Ser Gln Lys Arg Gly Arg Ser Arg Ser Arg Ser Arg Arg Asn Ala Asp
            20                  25                  30

Ile Pro Leu Ser Tyr Phe Asn Pro Ile Thr His Glu Gly Lys Lys Pro
        35                  40                  45

Phe Trp Thr Val Ala Pro Lys Asp Phe Val Pro Ile Gly Lys Gly Asn
    50                  55                  60

Lys Asp Gln Gln Val Gly Tyr Trp Asn Arg Gln Gln Arg Tyr Arg Ile
65                  70                  75                  80

Gln Lys Gly Gln Lys Val Asp Leu Pro Asp Arg Trp Phe Phe Tyr Tyr
                85                  90                  95

Leu Gly Thr Gly Pro His Ser Asn Ala Lys Phe Lys Asp Arg Ile Glu
            100                 105                 110

Gly Val Phe Trp Val Ala Arg
        115

<210> SEQ ID NO 4
<211> LENGTH: 628
<212> TYPE: DNA
<213> ORGANISM: Enteric coronavirus

<400> SEQUENCE: 4
tggataaggt taatgagtgc gtgcgttcac agtctagtag gtttggtttc tgtggcaacg      60
gcactcactt gttttcttta gctaatgctg cacctagtgg tatcatgcta tttcatacag     120
tcctagtgcc cacgtcttac acaagtgtaa cagcgtggtc tggcatttgt tttgataacg     180
ttggtttgat tgtcaaggat gtttcgttga cgttgtttaa aactcatgat gataaattct     240
acttgacacc acgtactatg tatgagccgc gtgtcgcgac tagcgcagat ttcgtgcgaa     300
ttaatagctg tgccactact tttgttaatg ccactgctac agagctacct aatattatac     360
ctgattatat tgatgttaat aagacagtcc aagacatgct agagcagtat aagcccaatt     420
ggacagtacc aaatttatcc cttgacttgt tcaatctaac atacttaaat ctcacgggtg     480
agattaatga tttggagaac aggtctgcta ccttgcaaca aactgttgtc gaattacagg     540
ttttaattga taatattaat ggaactcttg taaatcttga gtggcttaac acaattgaaa     600
catacgttaa gtggccatgg tacgtctg                                        628

<210> SEQ ID NO 5
<211> LENGTH: 208
<212> TYPE: PRT
<213> ORGANISM: Enteric coronavirus

<400> SEQUENCE: 5

Asp Lys Val Asn Glu Cys Val Arg Ser Gln Ser Ser Arg Phe Gly Phe
1               5                   10                  15

Cys Gly Asn Gly Thr His Leu Phe Ser Leu Ala Asn Ala Ala Pro Ser
```

-continued

```
                   20                  25                  30
Gly Ile Met Leu Phe His Thr Val Leu Val Pro Thr Ser Tyr Thr Ser
        35                  40                  45

Val Thr Ala Trp Ser Gly Ile Cys Phe Asp Asn Val Gly Leu Ile Val
50                  55                  60

Lys Asp Val Ser Leu Thr Leu Phe Lys Thr His Asp Lys Phe Tyr
65                  70                  75                  80

Leu Thr Pro Arg Thr Met Tyr Glu Pro Arg Val Ala Thr Ser Ala Asp
                85                  90                  95

Phe Val Arg Ile Asn Ser Cys Ala Thr Thr Phe Val Asn Ala Thr Ala
                100                 105                 110

Thr Glu Leu Pro Asn Ile Ile Pro Asp Tyr Ile Asp Val Asn Lys Thr
                115                 120                 125

Val Gln Asp Met Leu Glu Gln Tyr Lys Pro Asn Trp Thr Val Pro Asn
                130                 135                 140

Leu Ser Leu Asp Leu Phe Asn Leu Thr Tyr Leu Asn Leu Thr Gly Glu
145                 150                 155                 160

Ile Asn Asp Leu Glu Asn Arg Ser Ala Thr Leu Gln Gln Thr Val Val
                165                 170                 175

Glu Leu Gln Val Leu Ile Asp Asn Ile Asn Gly Thr Leu Val Asn Leu
                180                 185                 190

Glu Trp Leu Asn Thr Ile Glu Thr Tyr Val Lys Trp Pro Trp Tyr Val
                195                 200                 205
```

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
ggakaaggtk aatgartgyg t    21

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
ccakacvtac cawggccayt t    21

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
ctcgagcgac ccagamgacw ccktc    25

<210> SEQ ID NO 9
<211> LENGTH: 27
<212> TYPE: DNA
<213> ORGANISM: Artificial Sequence
<220> FEATURE:
<223> OTHER INFORMATION: Synthetic

```
<400> SEQUENCE: 9
gactagttgg tggagwttta ayccwga                                    27

<210> SEQ ID NO 10
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: n is a, c, g, or t

<400> SEQUENCE: 10
actcarwtra atytnaaata ygc                                        23

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
tcacayttwg gatartccca                                            20

<210> SEQ ID NO 12
<211> LENGTH: 251
<212> TYPE: DNA
<213> ORGANISM: Enteric coronavirus

<400> SEQUENCE: 12
actcagttga atctgaaata tgccatatca ggtaaggcac gagctcgtac tgttggtggt    60
gtgtcacttt tgtcaactat gaccacaaga cagtatcatc agaaacactt aaagcctatt   120
gccgccatgc gtaacgctac agttgtcatt ggtacagcca agttttacgg cggatgggac   180
gatatgttaa agaatttgat gcgtgacgtt gataatggct gtcttatggg ttgggattat   240
ccaaaatgtg a                                                      251

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
atggctgtct tatgggttgc c                                          21

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
gccagaccac gctgttacac t                                          21

<210> SEQ ID NO 15
<211> LENGTH: 628
<212> TYPE: DNA
<213> ORGANISM: Enteric coronavirus
```

<400> SEQUENCE: 15

```
ggataaggtt aatgagtgcg tgcgttcaca gtctagtagg tttggttcct gtggcaacgg    60
cactcacttg ttttctttag ctaatgctgc acctagtggt atcatgctat ttcatacagt   120
cctagtgccc acgtcttaca caagtgtaac agcgtggtct ggcatttgtt ttgataacgt   180
tggtttgatt gtcaaggatg tttcgttgac gttgtttaaa actcatgatg ataaattcta   240
cttgacacca cgtactatgt atgagccgcg agtcgcgact agtgcagatt tcgtgcgaat   300
taatagctgt gccactactt tgttaatgc cactgttaca gatctaccta atattatacc    360
tgattatatt gatgttaata agacagtcca agacatgcta gagcagtata agcccaattg   420
gacagtacca aatttatccc ttgacttgtt caatctaaca tacttaaatc tcacgggtga   480
gattaacgat ttggagaaca ggtctgtcac cttgcaacaa actgttgtcg aattacaggc   540
tttaattgct aacatcaatg gcacgcttgt taaccttgaa tggcttaaca gagttgaaac   600
atatgttaag tggccatggt acgtatgg                                      628
```

<210> SEQ ID NO 16
<211> LENGTH: 2496
<212> TYPE: DNA
<213> ORGANISM: Enteric coronavirus

<400> SEQUENCE: 16

```
gactagttgg tggagtttta accctgaaac caacgcaatc ttgtgtctta gtgcagtagg    60
aaaaagattt gtattaccac taatggtgc gcctacaggt gttacgttga cacttttgtc    120
aggtaactta tatgctgaag gcttcaaggt tggaagtggt gtaaatgtcg ataacctacc   180
caagtacatt atggtagcca cacctggtaa tactattata tatcaccaag ttggcaagtc   240
tcttaaagca tccagtgcga ctggttggtc atactatgtc cgagctaaag caggcgatta   300
ctcaacagaa gcaagacaag atcatttgag tgaaacacgaa aaactgttac atatggtata   360
agaactaaac ttctatcatg gctggaaacg gacaacgtgt taactggggg gacgaacctg   420
ctccttcaca gaagcgtggt cgttctcgtt cccgttcccg ccgtaatgct gatataccat   480
tgtcatattt caaccctatt acccatgaag gtaagaagcc cttttggact gtagcaccaa   540
agatttcgt gcctattggt aagggaaata aggaccaaca agtaggttat tggaatagac    600
agcaacgtta ccgcattcaa aagggtcaaa agtggactt accagacagg tggttctttt    660
actacctagg aactggtcca catagcaatg ctaaatttaa ggaccgtatt gacggagttt   720
tctgggttgg aaagaatggt gctaaaactg tgcctacagg attaggaacg cgtggcacca   780
accaacagtc tcttgacctt aaatttgatg gtaacgtgcc taatgatttc aaattagaac   840
aaaatgttgg gtctagaaac aactctaggt ctcgatctag aggaaggtct aagtccaaca   900
atagatccaa taacaataac agtaacagtg gtgatattgc cacagctgtt gttgcagctt   960
tagctcaaat gggttttgct cccaaagaca cacagaagaa taagtcccgc tctaaatcta  1020
gggataggtc taaatccaga gaaaaaccta ttcctaacaa tgagaacaag cactcatgga  1080
agaaaacacc tggtaaagga gaggtcgagt ctatgtttgg aaaccgtaga cctgaggcaa  1140
attttggcaa tgcagactta gttaaggctg gcagtgcaga tatacattac cctcaactag  1200
ctgagatggt tcctagtaac gccgccattt tatttggagg tgagtggact tctaaagaag  1260
agggtgatga tgttgtctta actgttaagt acagttataa agtgcctaag ggtgataaga  1320
caactgcatt tttgcaacac attaacgcct acacaaagcc ttcagatatt gtcaaagaac  1380
```

-continued

```
aacgttctcg atctaaatcc agagaacgtc ctcaaatccc tgtaccttcc aatagtgcag      1440
agactgaaaa ttacactgat gtgtttgatg agaatgttga aattattgat gaactaaact      1500
aaccatttct atgagttcta gcttaataac aatctttagt ggtaaaattt ggttttctct      1560
acctagatct tttaaagatt ggatagtatc taaagtcata ttcaaggcac ctgctggagg      1620
caaagtcaaa ccagactacc gccgcagagc tttgttaaac agtcataaca atcatgttaa      1680
ttctatgtct gttagttctg tctcttttt caaattcttt agggcaagaa gatgacaagc       1740
atcaacatcc cacatataac tgggaaagat tagattattt tgaaggttcc tacatcgaaa      1800
ttgataaatc tgtgatttta tcattaccac ttgacgccaa attacattgt ggtttggttg      1860
atggtgtttt gtgcaagttc ccaggttttg aagctgcata tgatgatcat gtagactatt      1920
atttagatgt agactcacct ttctacaggt ttgtgaacac cttctacgtg gctaaattca      1980
tagatggtaa gtttgacaat cgtgccactc tgaagtttct accacgtact agcaaagaca      2040
agatgcttgt tattggttgt ggtctcaatg accctcttct agacttgcct tttggtaccc      2100
aaatctataa tgatgtggac atgactctta agtcgacca tgtgccttgc actaacagac       2160
ggtattttgt taagtactgt cctggtggtc ccaatcattt ttgctttaaa gataaattgg      2220
taatcagaag gtttagagca ttttttccctg tgtctaataa taataaaatt gaacatgttg     2280
atttataaga agatcttcgg gcgagtaccg ttagatctac tcttacacag aatggtaagc      2340
acgtatctat gtagggtgta agtaactcat agatatatta ggaagtttag attgaactaa      2400
tcaatactag attgaaaaat tgagagtaat ttaaagatcc gcttagacga gccaacaatg      2460
gaagggctca acttttggat actagtcaac ttgttt                                2496
```

<210> SEQ ID NO 17
<211> LENGTH: 374
<212> TYPE: PRT
<213> ORGANISM: Enteric coronavirus

<400> SEQUENCE: 17

```
Met Ala Gly Asn Gly Gln Arg Val Asn Trp Gly Asp Glu Pro Ala Pro
1               5                   10                  15

Ser Gln Lys Arg Gly Arg Ser Arg Ser Arg Ser Arg Asn Ala Asp
                20                  25                  30

Ile Pro Leu Ser Tyr Phe Asn Pro Ile Thr His Glu Gly Lys Lys Pro
            35                  40                  45

Phe Trp Thr Val Ala Pro Lys Asp Phe Val Pro Ile Gly Lys Gly Asn
        50                  55                  60

Lys Asp Gln Gln Val Gly Tyr Trp Asn Arg Gln Arg Tyr Arg Ile
65                  70                  75                  80

Gln Lys Gly Gln Lys Val Asp Leu Pro Asp Arg Trp Phe Phe Tyr Tyr
                85                  90                  95

Leu Gly Thr Gly Pro His Ser Asn Ala Lys Phe Lys Asp Arg Ile Asp
            100                 105                 110

Gly Val Phe Trp Val Gly Lys Asn Gly Ala Lys Thr Val Pro Thr Gly
        115                 120                 125

Leu Gly Thr Arg Gly Thr Asn Gln Gln Ser Leu Asp Leu Lys Phe Asp
    130                 135                 140

Gly Asn Val Pro Asn Asp Phe Lys Leu Glu Gln Asn Val Gly Ser Arg
145                 150                 155                 160

Asn Asn Ser Arg Ser Arg Ser Arg Gly Arg Ser Lys Ser Asn Asn Arg
                165                 170                 175
```

```
                                    -continued
Ser Asn Asn Asn Asn Ser Asn Ser Gly Asp Ile Ala Thr Ala Val Val
            180                 185                 190

Ala Ala Leu Ala Gln Met Gly Phe Ala Pro Lys Asp Thr Gln Lys Asn
        195                 200                 205

Lys Ser Arg Ser Lys Ser Arg Asp Arg Ser Lys Ser Arg Glu Lys Pro
    210                 215                 220

Ile Pro Asn Asn Glu Asn Lys His Ser Trp Lys Lys Thr Pro Gly Lys
225                 230                 235                 240

Gly Glu Val Glu Ser Met Phe Gly Asn Arg Arg Pro Glu Ala Asn Phe
                245                 250                 255

Gly Asn Ala Asp Leu Val Lys Ala Gly Ser Ala Asp Ile His Tyr Pro
            260                 265                 270

Gln Leu Ala Glu Met Val Pro Ser Asn Ala Ala Ile Leu Phe Gly Gly
        275                 280                 285

Glu Trp Thr Ser Lys Glu Gly Asp Asp Val Val Leu Thr Val Lys
290                 295                 300

Tyr Ser Tyr Lys Val Pro Lys Gly Asp Lys Thr Thr Ala Phe Leu Gln
305                 310                 315                 320

His Ile Asn Ala Tyr Thr Lys Pro Ser Asp Ile Val Lys Glu Gln Arg
                325                 330                 335

Ser Arg Ser Lys Ser Arg Glu Arg Pro Gln Ile Pro Val Pro Ser Asn
            340                 345                 350

Ser Ala Glu Thr Glu Asn Tyr Thr Asp Val Phe Asp Glu Asn Val Glu
        355                 360                 365

Ile Ile Asp Glu Leu Asn
    370

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
acaggtggtt cttttactac c                                               21

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
tgtaggcaca gttttagcac                                                 20
```

We claim:

1. A purified oligonucleotide having a nucleic acid sequence SEQ ID NO: 16 or a portion thereof, said portion comprising a nucleic acid sequence of more than 30 nucleotides.

2. The oligonucleotide of claim 1, wherein said nucleic acid sequence is SEQ ID NO: 18.

3. The oligonucleotide of claim 1, wherein said nucleic acid sequence is SEQ ID NO: 19.

4. The oligonucleotide of claim 1, wherein the sequence is operably linked to a heterologous promoter.

5. A vector comprising the oligonucleotide of claim 1.

6. An isolated host cell comprising the vector of claim 5.

7. The host cell of claim 6, wherein the host cell is selected from the group consisting of animal and plant cells.

* * * * *